US011071498B2

United States Patent
Connor

(10) Patent No.: US 11,071,498 B2
(45) Date of Patent: Jul. 27, 2021

(54) SMART CLOTHING WITH INERTIAL, STRAIN, AND ELECTROMYOGRAPHIC SENSORS FOR HUMAN MOTION CAPTURE

(71) Applicant: Robert A. Connor, St. Paul, MN (US)

(72) Inventor: Robert A. Connor, St. Paul, MN (US)

(73) Assignee: Medibotics LLC, St. Paul, MN (US)

( * ) Notice: Subject to any disclaimer, the term of this patent is extended or adjusted under 35 U.S.C. 154(b) by 82 days.

(21) Appl. No.: 16/751,245

(22) Filed: Jan. 24, 2020

(65) Prior Publication Data

US 2020/0163621 A1 May 28, 2020

Related U.S. Application Data

(63) Continuation-in-part of application No. 16/543,056, filed on Aug. 16, 2019, now Pat. No. 10,839,202, and a continuation-in-part of application No. 16/017,439, filed on Jun. 25, 2018, now Pat. No. 10,921,886, said application No. 16/543,056 is a continuation-in-part of application No. 16/010,448, filed on Jun. 16, 2018, now Pat. No. 10,602,965, application No. 16/751,245, which is a continuation-in-part of application No. 16/010,448, filed on Jun. 16, 2018, now Pat. No. 10,602,965, said application No. 16/017,439 is a continuation-in-part of application No. 16/010,448, filed on Jun. 16, 2018, now Pat. No. 10,602,965, and a continuation-in-part of application No. 15/725,330, filed on Oct. 5, 2017, now Pat. No. 10,607,507, said application No. 16/010,448 is a
(Continued)

(51) Int. Cl.
*A61B 5/00* (2006.01)
*A61B 5/11* (2006.01)
*A41D 1/00* (2018.01)
*A61B 5/24* (2021.01)
*A61B 5/389* (2021.01)

(52) U.S. Cl.
CPC ............ *A61B 5/6804* (2013.01); *A41D 1/002* (2013.01); *A61B 5/11* (2013.01); *A61B 5/24* (2021.01); *A61B 5/389* (2021.01); *A61B 5/7278* (2013.01); *A61B 2503/10* (2013.01); *A61B 2503/12* (2013.01); *A61B 2562/0219* (2013.01); *A61B 2562/0261* (2013.01); *A61B 2562/06* (2013.01)

(58) Field of Classification Search
CPC ......... A61B 5/6804; A61B 5/389; A61B 5/24; A61B 5/11; A61B 5/7278; A61B 2503/10; A61B 2503/12; A61B 2562/0219; A61B 2562/06; A41D 1/002
See application file for complete search history.

(56) References Cited

U.S. PATENT DOCUMENTS

| 6,145,551 A | 11/2000 | Jayaraman et al. |
| 6,315,009 B1 | 11/2001 | Jayaraman et al. |

(Continued)

*Primary Examiner* — Max H Noori

(57) ABSTRACT

This invention is smart clothing which enables human motion capture through combined analysis of data from inertial sensors, strain (or bend) sensors, and electromyographic (EMG) sensors. In a preferred embodiment, a first inertial motion sensor is located proximal to the body joint, a second inertial sensor is located distal to the body joint, two strain sensors span the body joint in different configurations, and an electromyographic (EMG) sensor collects data concerning electromagnetic energy from the muscles which move the body joint.

3 Claims, 1 Drawing Sheet

Related U.S. Application Data continuation-in-part of application No. 15/702,081, filed on Sep. 12, 2017, now Pat. No. 10,716,510, application No. 16/751,245, which is a continuation-in-part of application No. 15/702,081, filed on Sep. 12, 2017, now Pat. No. 10,716,510, said application No. 16/010,448 is a continuation-in-part of application No. 15/227,254, filed on Aug. 3, 2016, now Pat. No. 10,321,873, said application No. 15/702,081 is a continuation-in-part of application No. 15/227,254, filed on Aug. 3, 2016, now Pat. No. 10,321,873, which is a continuation-in-part of application No. 15/130,995, filed on Apr. 17, 2016, now Pat. No. 9,891,718, and a continuation-in-part of application No. 15/079,447, filed on Mar. 24, 2016, now Pat. No. 10,234,934, said application No. 16/017,439 is a continuation-in-part of application No. 14/795,373, filed on Jul. 9, 2015, now abandoned, said application No. 15/702,081 is a continuation-in-part of application No. 14/795,373, filed on Jul. 9, 2015, now abandoned, said application No. 15/227,254 is a continuation-in-part of application No. 14/736,652, filed on Jun. 11, 2015, now abandoned, said application No. 14/795,373 is a continuation-in-part of application No. 14/736,652, filed on Jun. 11, 2015, now abandoned, said application No. 15/079,447 is a continuation-in-part of application No. 14/664,832, filed on Mar. 21, 2015, now Pat. No. 9,582,072, said application No. 14/736,652 is a continuation-in-part of application No. 14/664,832, filed on Mar. 21, 2015, now Pat. No. 9,582,072, said application No. 15/227,254 is a continuation-in-part of application No. 14/664,832, filed on Mar. 21, 2015, now Pat. No. 9,582,072, which is a continuation-in-part of application No. 14/463,741, filed on Aug. 20, 2014, now Pat. No. 9,588,582, said application No. 15/079,447 is a continuation-in-part of application No. 14/463,741, filed on Aug. 20, 2014, now Pat. No. 9,588,582.

(60) Provisional application No. 62/797,266, filed on Jan. 26, 2019, provisional application No. 62/727,798, filed on Sep. 6, 2018, provisional application No. 62/683,237, filed on Jun. 11, 2018, provisional application No. 62/538,793, filed on Jul. 30, 2017, provisional application No. 62/449,735, filed on Jan. 24, 2017, provisional application No. 62/357,957, filed on Jul. 2, 2016, provisional application No. 62/187,906, filed on Jul. 2, 2015, provisional application No. 62/182,473, filed on Jun. 20, 2015, provisional application No. 62/150,886, filed on Apr. 22, 2015, provisional application No. 62/100,217, filed on Jan. 6, 2015, provisional application No. 62/086,053, filed on Dec. 1, 2014, provisional application No. 62/065,032, filed on Oct. 17, 2014, provisional application No. 62/014,747, filed on Jun. 20, 2014, provisional application No. 61/976,650, filed on Apr. 8, 2014, provisional application No. 61/878,893, filed on Sep. 17, 2013.

(56) References Cited

U.S. PATENT DOCUMENTS

| | | |
|---|---|---|
| 6,381,482 B1 | 4/2002 | Jayaraman et al. |
| 6,487,906 B1 | 12/2002 | Hock |
| 6,687,523 B1 | 2/2004 | Jayaramen et al. |
| 6,970,731 B1 | 11/2005 | Jayaraman et al. |
| 7,771,318 B2 | 8/2010 | Narayanaswami |
| 7,850,574 B2 | 12/2010 | Narayanaswami |
| 7,981,057 B2 | 7/2011 | Stewart |
| 8,162,857 B2 | 4/2012 | Lanfermann et al. |
| 8,291,779 B2 | 10/2012 | Helmer et al. |
| 8,348,865 B2 | 1/2013 | Jeong et al. |
| 8,945,328 B2 | 2/2015 | Longinotti-Buitoni et al. |
| 8,948,839 B1 | 2/2015 | Longinotti-Buitoni et al. |
| 9,043,004 B2 | 5/2015 | Casillas et al. |
| 9,322,121 B2 | 4/2016 | Dunne et al. |
| 9,498,128 B2 | 11/2016 | Jayalath et al. |
| 9,546,921 B2 | 1/2017 | McMillen et al. |
| 9,612,102 B2 | 4/2017 | Reese et al. |
| 9,652,101 B2 | 5/2017 | McMillen |
| 9,696,833 B2 | 7/2017 | McMillen |
| 9,700,238 B2 | 7/2017 | Stewart |
| 9,710,060 B2 | 7/2017 | McMillen et al. |
| 9,753,568 B2 | 9/2017 | McMillen |
| 9,797,791 B2 | 10/2017 | Vogt et al. |
| 9,816,799 B2 | 11/2017 | Keller et al. |
| 9,816,800 B2 | 11/2017 | O'Brien et al. |
| 9,817,440 B2 | 11/2017 | Longinotti-Buitoni et al. |
| 9,839,394 B2 | 12/2017 | Casillas et al. |
| 9,841,330 B2 | 12/2017 | Casillas et al. |
| 9,850,600 B2 | 12/2017 | Gal |
| 9,874,431 B2 | 1/2018 | Reese |
| 9,885,621 B2 | 2/2018 | Dunne et al. |
| 9,913,611 B2 | 3/2018 | Wiebe et al. |
| 9,965,076 B2 | 5/2018 | McMillen |
| 9,986,771 B2 | 6/2018 | Longinotti-Buitoni et al. |
| 10,045,439 B2 | 8/2018 | Longinotti-Buitoni et al. |
| 10,065,074 B1 | 9/2018 | Hoang et al. |
| 10,067,007 B2 | 9/2018 | Keller et al. |
| 10,105,098 B2 | 10/2018 | Wiebe et al. |
| 10,119,208 B2 | 11/2018 | Mcmaster |
| 10,139,293 B2 | 11/2018 | Casillas et al. |
| 10,143,405 B2 | 12/2018 | Jayalath et al. |
| 10,159,440 B2 | 12/2018 | Longinotti-Buitoni et al. |
| 10,172,541 B2 | 1/2019 | Liao et al. |
| 10,197,459 B2 | 2/2019 | Keller et al. |
| 10,228,231 B2 | 3/2019 | O'Brien et al. |
| 10,240,265 B2 | 3/2019 | Mcmaster |
| 10,258,092 B2 | 4/2019 | Longinotti-Buitoni et al. |
| 10,268,315 B2 | 4/2019 | Mcmillen |
| 10,274,384 B2 | 4/2019 | Dunne et al. |
| 10,282,011 B2 | 5/2019 | Mcmillen |
| 10,288,507 B2 | 5/2019 | Mcmillen et al. |
| 10,292,652 B2 | 5/2019 | Berg et al. |
| 10,321,832 B2 | 6/2019 | Berg et al. |
| 10,362,958 B2 | 7/2019 | Morun et al. |
| 10,362,989 B2 | 7/2019 | Mcmillen et al. |
| 10,378,975 B1 | 8/2019 | Sun |
| 10,413,219 B2 | 9/2019 | Jayalath et al. |
| 10,429,928 B2 | 10/2019 | Morun et al. |
| 10,458,866 B1 | 10/2019 | Sun |
| 10,462,898 B2 | 10/2019 | Longinotti-Buitoni et al. |
| 10,488,936 B2 | 11/2019 | Baranski et al. |
| 10,502,643 B2 | 12/2019 | Keller et al. |
| 10,527,507 B2 | 1/2020 | Wood et al. |
| 10,535,278 B2 | 1/2020 | Chahine |
| 11,016,111 B1 * | 5/2021 | Chuang ............... G01P 1/00 |
| 2010/0036288 A1 | 2/2010 | Lanfermann et al. |
| 2011/0125064 A1 * | 5/2011 | Shyr ............... A61B 5/02438 |
| | | 600/595 |
| 2012/0188158 A1 | 7/2012 | Tan et al. |
| 2013/0285577 A1 | 10/2013 | O'Brien et al. |
| 2014/0135593 A1 | 5/2014 | Jayalth et al. |
| 2014/0142459 A1 | 5/2014 | Jayalth et al. |
| 2014/0238151 A1 | 8/2014 | Dunne et al. |
| 2014/0238153 A1 | 8/2014 | Wood et al. |
| 2014/0240103 A1 | 8/2014 | Lake et al. |
| 2014/0240223 A1 | 8/2014 | Lake et al. |
| 2014/0318699 A1 | 10/2014 | Longinotti-Buitoni et al. |
| 2015/0040282 A1 | 2/2015 | Longinotti-Buitoni et al. |
| 2015/0123647 A1 | 5/2015 | Gisby et al. |
| 2015/0148619 A1 | 5/2015 | Berg et al. |
| 2015/0230719 A1 | 8/2015 | Berg et al. |
| 2015/0305677 A1 | 10/2015 | Berg et al. |

(56) References Cited

U.S. PATENT DOCUMENTS

| | | |
|---|---|---|
| 2015/0331533 A1 | 11/2015 | McMillen |
| 2015/0359455 A1 | 12/2015 | Hahami et al. |
| 2015/0359485 A1 | 12/2015 | Berg et al. |
| 2015/0366504 A1* | 12/2015 | Connor .............. A61B 5/6804 600/301 |
| 2016/0033255 A1 | 2/2016 | Reese |
| 2016/0070347 A1 | 3/2016 | McMillen et al. |
| 2016/0091980 A1 | 3/2016 | Baranski et al. |
| 2016/0128632 A1 | 5/2016 | Wiebe et al. |
| 2016/0238368 A1 | 8/2016 | O'Brien et al. |
| 2016/0287175 A1 | 10/2016 | Coleman et al. |
| 2016/0305759 A1 | 10/2016 | Reese et al. |
| 2016/0338644 A1* | 11/2016 | Connor .............. A61B 5/1071 |
| 2017/0035354 A1 | 2/2017 | Jayalath et al. |
| 2017/0036066 A1 | 2/2017 | Chahine |
| 2017/0038881 A1 | 2/2017 | McMillen |
| 2017/0074637 A1 | 3/2017 | Reese |
| 2017/0086711 A1 | 3/2017 | Liao et al. |
| 2017/0168567 A1 | 6/2017 | Reese et al. |
| 2017/0171965 A1 | 6/2017 | Youn et al. |
| 2017/0191819 A1 | 7/2017 | O'Brien et al. |
| 2017/0196513 A1 | 7/2017 | Longinotti-Buitoni et al. |
| 2017/0265810 A1 | 9/2017 | Van De Vyver |
| 2017/0303853 A1 | 10/2017 | McMillen et al. |
| 2017/0347721 A1 | 12/2017 | Greenspan et al. |
| 2018/0049698 A1 | 2/2018 | Berg et al. |
| 2018/0051974 A1 | 2/2018 | O'Brien et al. |
| 2018/0067516 A1 | 3/2018 | Longinotti-Buitoni et al. |
| 2018/0279951 A1 | 10/2018 | Asnis et al. |
| 2018/0376586 A1 | 12/2018 | Longinotti-Buitoni |
| 2019/0046114 A1 | 2/2019 | Bogdanovich et al. |
| 2019/0059461 A1 | 2/2019 | Walker |
| 2019/0069612 A1* | 3/2019 | Hyde .............. A44B 11/2546 |
| 2019/0117157 A1 | 4/2019 | Hu et al. |
| 2019/0132948 A1 | 5/2019 | Longinotti-Buitoni et al. |
| 2019/0145752 A1 | 5/2019 | Zhu et al. |
| 2019/0151713 A1 | 5/2019 | Berg et al. |
| 2019/0185672 A1 | 6/2019 | Boland et al. |
| 2019/0220099 A1 | 7/2019 | Baranski et al. |
| 2019/0228330 A1 | 7/2019 | Kaifosh et al. |
| 2019/0261874 A1 | 8/2019 | Berg et al. |
| 2019/0290198 A1 | 9/2019 | Belson et al. |
| 2019/0310713 A1 | 10/2019 | Wang et al. |
| 2019/0342993 A1 | 11/2019 | Ahn et al. |
| 2019/0364983 A1 | 12/2019 | Nakajima et al. |
| 2019/0390985 A1 | 12/2019 | Kwok et al. |
| 2020/0000378 A1 | 1/2020 | Jayalath et al. |
| 2020/0008715 A1 | 1/2020 | Schroeck et al. |

\* cited by examiner

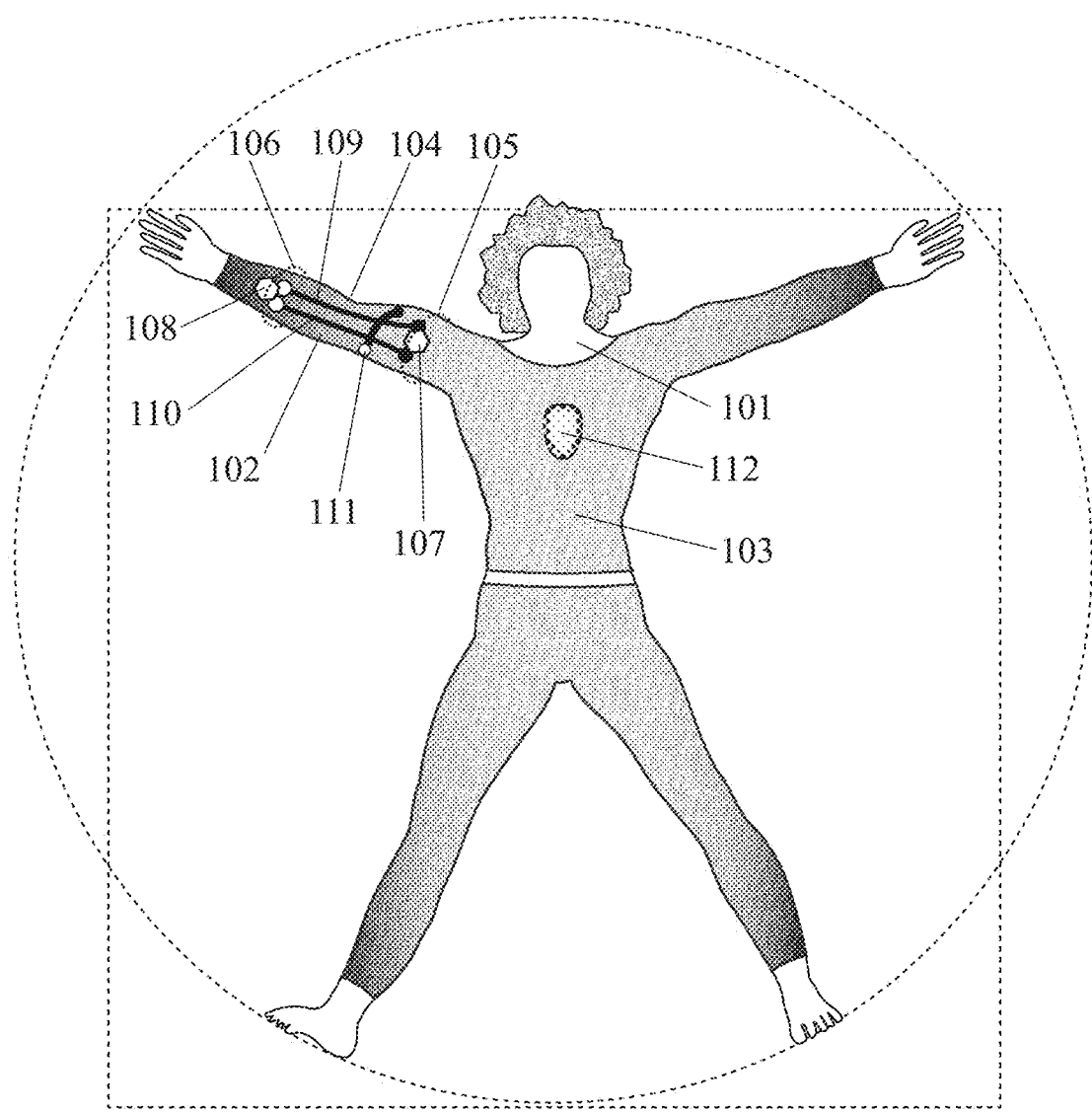

SMART CLOTHING WITH INERTIAL, STRAIN, AND ELECTROMYOGRAPHIC SENSORS FOR HUMAN MOTION CAPTURE

CROSS-REFERENCE TO RELATED APPLICATIONS

This application is: a continuation in part of patent application Ser. No. 16/543,056 filed on 2019 Aug. 16; claims the priority benefit of provisional patent application 62/797,266 filed on 2019 Jan. 26; is a continuation in part of patent application Ser. No. 16/017,439 filed on 2018 Jun. 25; is a continuation in part of patent application Ser. No. 16/010,448 filed on 2018 Jun. 16; and is a continuation in part of patent application Ser. No. 15/702,081 filed on 2017 Sep. 12.

Application Ser. No. 16/543,056 claimed the priority benefit of provisional patent application 62/797,266 filed on 2019 Jan. 26. Application Ser. No. 16/543,056 claimed the priority benefit of provisional patent application 62/727,798 filed on 2018 Sep. 6. Application Ser. No. 16/543,056 was a continuation in part of patent application Ser. No. 16/010,448 filed on 2018 Jun. 16.

Application Ser. No. 16/017,439 was a continuation in part of patent application Ser. No. 16/010,448 filed on 2018 Jun. 16. Application Ser. No. 16/017,439 claimed the priority benefit of provisional patent application 62/683,237 filed on 2018 Jun. 11. Application Ser. No. 16/017,439 was a continuation in part of patent application Ser. No. 15/725,330 filed on 2017 Oct. 5. Application Ser. No. 16/017,439 was a continuation in part of patent application Ser. No. 14/795,373 filed on 2015 Jul. 9.

Application Ser. No. 16/010,448 claimed the priority benefit of provisional patent application 62/683,237 filed on 2018 Jun. 11. Application Ser. No. 16/010,448 claimed the priority benefit of provisional patent application 62/538,793 filed on 2017 Jul. 30. Application Ser. No. 16/010,448 was a continuation in part of patent application Ser. No. 15/702,081 filed on 2017 Sep. 12. Application Ser. No. 16/010,448 was a continuation in part of patent application Ser. No. 15/227,254 filed on 2016 Aug. 3 which is now U.S. Pat. No. 10,321,873 issued on 2019 Jun. 18.

Application Ser. No. 15/702,081 was a continuation in part of patent application Ser. No. 14/795,373 filed on 2015 Jul. 9. Application Ser. No. 15/702,081 claimed the priority benefit of provisional patent application 62/538,793 filed on 2017 Jul. 30. Application Ser. No. 15/702,081 claimed the priority benefit of provisional patent application 62/449,735 filed on 2017 Jan. 24. Application Ser. No. 15/702,081 was a continuation in part of patent application Ser. No. 15/227,254 filed on 2016 Aug. 3 which is now U.S. Pat. No. 10,321,873 issued on 2019 Jun. 18.

Application Ser. No. 15/227,254 claimed the priority benefit of provisional patent application 62/357,957 filed on 2016 Jul. 2. Application Ser. No. 15/227,254 was a continuation in part of patent application Ser. No. 14/736,652 filed on 2015 Jun. 11. Application Ser. No. 15/227,254 was a continuation in part of patent application Ser. No. 14/664,832 filed on 2015 Mar. 21 which is now U.S. Pat. No. 9,582,072 issued on 2017 Feb. 28. Application Ser. No. 15/227,254 was a continuation in part of patent application Ser. No. 15/130,995 filed on 2016 Apr. 17 which is now U.S. Pat. No. 9,891,718 issued on 2018 Feb. 13. Application Ser. No. 15/227,254 was a continuation in part of patent application Ser. No. 15/079,447 filed on 2016 Mar. 24 which is now U.S. Pat. No. 10,234,934 issued on 2019 Mar. 19.

Application Ser. No. 15/130,995 claimed the priority benefit of provisional patent application 62/150,886 filed on 2015 Apr. 22. Application Ser. No. 15/079,447 claimed the priority benefit of provisional patent application 62/150,886 filed on 2015 Apr. 22. Application Ser. No. 15/079,447 was a continuation in part of patent application Ser. No. 14/664,832 filed on 2015 Mar. 21 which is now U.S. Pat. No. 9,582,072 issued on 2017 Feb. 28. Application Ser. No. 15/079,447 was a continuation in part of patent application Ser. No. 14/463,741 filed on 2014 Aug. 20 which is now U.S. Pat. No. 9,588,582 issued on 2017 Mar. 7.

Application Ser. No. 14/795,373 claimed the priority benefit of provisional patent application 62/187,906 filed on 2015 Jul. 2. Application Ser. No. 14/795,373 claimed the priority benefit of provisional patent application 62/182,473 filed on 2015 Jun. 20. Application Ser. No. 14/795,373 claimed the priority benefit of provisional patent application 62/086,053 filed on 2014 Dec. 1. Application Ser. No. 14/795,373 claimed the priority benefit of provisional patent application 62/065,032 filed on 2014 Oct. 17. Application Ser. No. 14/795,373 was a continuation in part of patent application Ser. No. 14/736,652 filed on 2015 Jun. 11.

Application Ser. No. 14/736,652 claimed the priority benefit of provisional patent application 62/100,217 filed on 2015 Jan. 6. Application Ser. No. 14/736,652 claimed the priority benefit of provisional patent application 62/014,747 filed on 2014 Jun. 20. Application Ser. No. 14/736,652 was a continuation in part of patent application Ser. No. 14/664,832 filed on 2015 Mar. 21 which is now U.S. Pat. No. 9,582,072 issued on 2017 Feb. 28. Application Ser. No. 14/664,832 claimed the priority benefit of provisional patent application 61/976,650 filed on 2014 Apr. 8. Application Ser. No. 14/664,832 was a continuation in part of patent application Ser. No. 14/463,741 filed on 2014 Aug. 20 which is now U.S. Pat. No. 9,588,582 issued on 2017 Mar. 7. Application Ser. No. 14/463,741 claimed the priority benefit of provisional patent application 61/878,893 filed on 2013 Sep. 17.

The entire contents of these applications are incorporated herein by reference.

FEDERALLY SPONSORED RESEARCH

Not Applicable

SEQUENCE LISTING OR PROGRAM

Not Applicable

BACKGROUND

Field of Invention

This invention relates to devices and methods for human motion capture.

INTRODUCTION

There are many potential applications for wearable devices such as smart clothing which can enable human motion capture. These potential applications include: athletic training and motion capture for sports which involve extensive lower-body motion (such as bicycling and soccer), extensive arm motion (such as tennis and golf), extensive lower-body motion (such as bicycling and running), extensive spinal motion, extensive forearm motion (such as tennis and golf), wrist motion (such as tennis, golf, and Frisbee), ankle motion (such as running and soccer), finger and hand motion (such as tennis, golf, baseball, and fencing), athletic performance measurement and improvement; and entertainment, gaming, and artistic applications (such as animated pictures, avatar animation, computer animation, computer gaming, dance instruction, dance performance, gaming input devices, graphical animation, motion capture, motion picture animation, motion pictures, movie making, performance arts, training and motion capture for playing musical instruments, virtual gaming, virtual reality); and health, fitness, and medical applications (such as avoidance of repeated motion injuries, biofeedback, biomechanical analysis, caloric expenditure measurement, caloric intake monitoring, cardiac function monitoring, congestive heart failure assessment, energy balance, ergonomic evaluation, fall prevention and detection, gait analysis, medical diagnosis, medical therapy, nutritional monitoring and improvement, orthopedic therapy, orthotic design and fitting, physical therapy, plethysmography, post-operative therapy, posture correction, pronation analysis, pulse monitoring, range of motion assessment, rehabilitation assessment, repetitive stress injury avoidance, respiratory function analysis, spinal injury avoidance, spinal motion assessment, telemedicine, telesurgery, virtual exercise, weight management); and human-computer interface and telecommunication (such as gesture recognition, telerobotics, telesurgery, telepresence, notifications, telecommunication, teleconferencing, telepresence, telerobotics, virtual commerce, and virtual reality interaction).

There are different types of sensors which can be incorporated into smart clothing for human motion capture, but each has limitations in addition to strengths. For example, inertial motion sensors do not require form-fitting clothing to measure motion and can measure relatively small motions, but can suffer from drift and not provide posture identification when first activated. Strain sensors can help to correct drift and can provide posture identification when first activated, but can be less accurate in loose-fitting clothing and for small motions. Electromyographic (EMG) sensors can provide information about muscle exertion and force that neither inertial sensors nor strain sensors can provide, but require close contact with a person's body and can be less accurate for measuring joint angles. There remains a need for accurate and unobtrusive smart clothing which enables ambulatory full-body human motion capture.

Review of the Relevant Art

Myant is a significant innovator with respect to clothing for human motion capture. Their work includes U.S. Pat. No. 10,535,278 (Chahine, Jan. 14, 2020, "Garment with Stretch Sensors") and U.S. patent application publication 20170036066 (Chahine, Feb. 9, 2017, "Garment with Stretch Sensors") which disclose a knitted or woven garment configured for sensing movement of an adjacent underlying body portion of a wearer of the garment via one or more sensors.

Another significant innovator with respect to clothing for human motion capture is L.I.F.E. Corporation. Their work includes U.S. Pat. No. 10,045,439 (Longinotti-Buitoni et al., Aug. 7, 2018, "Garments Having Stretchable and Conductive Ink"), U.S. Pat. No. 10,258,092 (Longinotti-Buitoni et al., Apr. 16, 2019, "Garments Having Stretchable and Conductive Ink"), U.S. Pat. No. 8,945,328 (Longinotti-Buitoni et al., Feb. 3, 2015, "Methods of Making Garments Having Stretchable and Conductive Ink"), U.S. Pat. No. 8,948,839 (Longinotti-Buitoni et al., Feb. 3, 2015, "Compression Garments Having Stretchable and Conductive Ink"), U.S. Pat. No. 9,817,440 (Longinotti-Buitoni et al., Nov. 14, 2017, "Garments Having Stretchable and Conductive Ink"), and U.S. Pat. No. 9,986,771 (Longinotti-Buitoni et al., Jun. 5, 2018, "Garments Having Stretchable and Conductive Ink"); and U.S. patent application publications 20180067516 (Longinotti-Buitoni et al., Mar. 8, 2018, "Garments Having Stretchable and Conductive Ink"), 20180376586 (Longinotti-Buitonii et al., Dec. 27, 2018, "Garments Having Stretchable and Conductive Ink"), 20170196513 (Longinotti-Buitoni et al., Jul. 13, 2017, "Garments Having Stretchable and Conductive Ink"), 20150040282 (Longinotti-Buitoni et al., Feb. 12, 2015, "Compression Garments Having Stretchable and Conductive Ink"), and 20140318699 (Longinotti-Buitoni et al., Oct. 30, 2014, "Methods of Making Garments Having Stretchable and Conductive Ink"), which disclose garments with stretchable conductive ink patterns. U.S. Pat. No. 10,159,440 (Longinotti-Buitoni et al., Dec. 25, 2018, "Physiological Monitoring Garments") and U.S. Pat. No. 10,462,898 (Longinotti-Buitoni et al., Oct. 29, 2019, "Physiological Monitoring Garments"), and U.S. patent application publication 20190132948 (Longinotti-Buitonii et al., May 2, 2019, "Physiological Monitoring Garments") disclose garments for detecting and monitoring physiological parameters such as respiration and cardiac parameters.

Another significant innovator with respect to clothing for human motion capture is StretchSense. Their work includes patent application publication 20130285577 (O'Brien et al., Oct. 31, 2013, "Dielectric Elastomer Self-Sensing Using Plane Approximation") which discloses a method for obtaining feedback parameters related to the state of a dielectric elastomer (DE). U.S. patent application publication 20170191819 (O'Brien et al., Jul. 6, 2017, "Electro-Mechanical Sensor") discloses an electrical sensor having an electrical capacitance which varies with mechanical deformation. U.S. Pat. No. 10,228,231 (O'Brien et al., Mar. 12, 2019, "Laminated Devices of Elastic Material Suitable for Dielectric Elastomer Sensing") discloses a laminated device of flexible and compliant layers of material, such as used to provide a dielectric elastomer sensor. U.S. Pat. No. 9,816,800 (O'Brien et al., Nov. 14, 2017, "Method of Fabrication of Laminates of Elastic Material Suitable for Dielectric Elastomer Sensing"), and U.S. patent application publications 20160238368 (O'Brien et al., Aug. 18, 2016, "Method of Fabrication of Laminates of Elastic Material Suitable for Dielectric Elastomer Sensing") and 20180051974 (O'Brien et al., Feb. 22, 2018, "Method of Fabrication of Laminates of Elastic Material Suitable for Dielectric Elastomer Sensing"), disclose a method of fabricating a laminate of flexible and compliant layers of material, such as used to provide a dielectric elastomer sensor. U.S. patent application publication 20150123647 (Gisby et al., May 7, 2015, "Self-Sensing Dielectric Elastomer Device") discloses circuits, systems and methods for dielectric elastomer device (DED) self-sensing.

Another significant innovator with respect to clothing for human motion capture is BeBop Sensors. Their work includes U.S. Pat. No. 9,753,568 (McMillen, Sep. 5, 2017, "Flexible Sensors and Applications") and U.S. Pat. No. 10,282,011 (McMillen, May 7, 2019, "Flexible Sensors and Applications"), and also U.S. patent application publications 20150331533 (McMillen, Nov. 19, 2015, "Flexible Sensors and Applications") and 20170038881 (McMillen, Feb. 9, 2017, "Flexible Sensors and Applications") which disclose wearable sensors with piezoresistive materials. U.S. Pat. No. 9,965,076 (McMillen, May 8, 2018, "Piezoresistive Sensors and Applications"), U.S. Pat. No. 9,546,921 (McMillen et al., Jan. 17, 2017, "Piezoresistive Sensors and Sensor Arrays"), U.S. Pat. No. 10,288,507 (McMillen et al., May 14, 2019, "Piezoresistive Sensors and Sensor Arrays"), and U.S. Pat. No. 9,696,833 (McMillen, Jul. 4, 2017, "Promoting Sensor Isolation and Performance in Flexible Sensor Arrays") disclose sensors with conductive traces on piezoresistive material with musical applications. U.S. Pat. No. 9,710,060 (McMillen et al., Jul. 18, 2017, "Sensor System Integrated with a Glove") and U.S. Pat. No. 10,362,989 (McMillen et al., Jul. 30, 2019, "Sensor System Integrated with a Glove"), and U.S. patent application publications 20160070347 (McMillen et al., Mar. 10, 2016, "Sensor System Integrated with a Glove") and 20170303853 (McMillen et al., Oct. 26, 2017, "Sensor System Integrated with a Glove") disclose sensor systems with piezoresistive material in gloves to measure hand motion. U.S. Pat. No. 9,652,101 (McMillen, May 16, 2017, "Two-Dimensional Sensor Arrays") and U.S. Pat. No. 10,268,315 (McMillen, Apr. 23, 2019, "Two-Dimensional Sensor Arrays") disclose two-dimensional sensor arrays made with piezoresistive material.

Another significant innovator with respect to clothing for human motion capture is Nike. Their work includes U.S. Pat. No. 9,043,004 (Casillas et al., May 26, 2015, "Apparel Having Sensor System"), 9839394 (Casillas et al., Dec. 12, 2017, "Apparel Having Sensor System"), U.S. Pat. No. 9,841,330 (Casillas et al., Dec. 12, 2017, "Apparel Having Sensor System"), and U.S. Pat. No. 10,139,293 (Casillas et al., Nov. 27, 2018, "Apparel Having Sensor System") which disclose a plurality of sensors formed of a polymeric material having a conductive particulate material dispersed therein and conductive leads connecting the sensors to a port. U.S. patent application publication 20190059461 (Walker, Feb. 28, 2019, "Sense-Enabled Apparel") discloses an apparel piece sized to be worn on a user and a sensor system integrated with the apparel piece.

Another significant innovator with respect to clothing for human motion capture is Mad Apparel (Athos). Their work includes patent application publication 20150305677 (Berg et al., Oct. 29, 2015, "Biometric Electrode System and Method of Manufacture") which discloses an electrode system for EMG sensors with a substrate comprising a reference region and a signal communication region. U.S. patent application publication 20150359485 (Berg et al., Dec. 17, 2015, "Biometric Signal Conduction System and Method of Manufacture") discloses EMG sensors with a flexible substrate including a first broad surface and a second broad surface opposing the first broad surface. U.S. Pat. No. 9,913,611 (Wiebe et al., Mar. 13, 2018, "Garment Integrated Sensing System and Method") and U.S. Pat. No. 10,105,098 (Wiebe et al., Oct. 23, 2018, "Garment Integrated Sensing System and Method"), and U.S. patent application publication 20160128632 (Wiebe et al., May 12, 2016, "Garment Integrated Sensing System and Method"), disclose wireless sensor interfaces coupled to a garment, wherein each sensor includes an electrode layer, a positional identifier, and a retention subsystem. U.S. patent application publication 20180049698 (Berg et al., Feb. 22, 2018, "Garment with Conductive Thread Exposed on Both Sides") discloses a garment made by bonding an adhesive to a first layer of fabric and a second layer of fabric. U.S. patent application publication 20180279951 (Asnis et al., Oct. 4, 2018, "Movement Compensation for Sensor-Equipped Athletic Garments") discloses an athletic garment includes connective segments that compensate for motion of an athlete wearing the athletic garment. U.S. patent application publication 20190151713 (Berg et al., May 23, 2019, "Printable Electronic Garment Conduit") discloses an athletic garment with printed EMG sensors. U.S. Pat. No. 10,292,652 (Berg et al., May 21, 2019, "System and Method for Monitoring Biometric Signals") and U.S. Pat. No. 10,321,832 (Berg et al., Jun. 18, 2019, "System and Method for Monitoring Biometric Signals"), and U.S. patent application publications 20150148619 (Berg et al., May 28, 2015, "System and Method for Monitoring Biometric Signals"), 20150230719 (Berg et al., Aug. 20, 2015, "System and Method for Monitoring Biometric Signals"), and 20190261874 (Berg et al., Aug. 29, 2019, "System and Method for Monitoring Biometric Signals") disclose a garment with a mounting module having an array of connection regions and biometric sensors. U.S. Pat. No. 9,498,128 (Jayalath et al., Nov. 22, 2016, "Wearable Architecture and Methods for Performance Monitoring, Analysis, and Feedback") and U.S. Pat. No. 10,413,219 (Jayalath et al., Sep. 17, 2019, "Wearable Architecture and Methods for Performance Monitoring, Analysis, and Feedback"), and U.S. patent application publications 20140135593 (Jayalth et al., May 15, 2014, "Wearable Architecture and Methods for Performance Monitoring, Analysis, and Feedback"), 20170035354 (Jayalath et al., Feb. 9, 2017, "Wearable Architecture and Methods for Performance Monitoring, Analysis, and Feedback"), and 20200000378 (Jayalath et al., Jan. 2, 2020, "Wearable Architecture and Methods for Performance Monitoring, Analysis, and Feedback"), disclose techniques, fabrics, materials, systems, sensors, EMG sensors, circuitry, algorithms and methods for wearable monitoring devices and associated exercise devices. U.S. Pat. No. 10,143,405 (Jayalath et al., Dec. 4, 2018, "Wearable Performance Monitoring, Analysis, and Feedback Systems and Methods") and U.S. patent application publication 20140142459 (Jayalath et al., May 22, 2014, "Wearable Performance Monitoring, Analysis, and Feedback Systems and Methods") disclose techniques, systems, sensors, circuitry, algorithms and methods for wearable monitoring devices.

Another significant innovator with respect to clothing for human motion capture is Georgia Tech. Their work includes U.S. Pat. No. 6,381,482 (Jayaraman et al., Apr. 30, 2002, "Fabric or Garment with Integrated Flexible Information Infrastructure") which discloses a modular electronic garment. U.S. Pat. No. 6,687,523 (Jayaramen et al., Feb. 3, 2004, "Fabric or Garment with Integrated Flexible Information Infrastructure for Monitoring Vital Signs Of Infants") discloses an infant garment which ensures a snug fit for the baby so that the sensors stay in place to minimize the risk of false alarms. U.S. Pat. No. 6,970,731 (Jayaraman et al., Nov. 29, 2005, "Fabric-Based Sensor for Monitoring Vital Signs") discloses a woven or knitted fabric-based sensor for monitoring vital signs or other electrical impulses. U.S. Pat. No. 6,315,009 (Jayaraman et al., Nov. 13, 2001, "Full-Fashioned Garment with Sleeves Having Intelligence Capability") discloses a full-fashioned weaving process for the production of a woven garment which can accommodate and include sleeves. U.S. Pat. No. 6,145,551 (Jayaraman et al., Nov. 14, 2000, "Full-Fashioned Weaving Process for Production of a Woven Garment with Intelligence Capability") discloses a full-fashioned weaving process for the production of a woven garment which can accommodate and include holes.

Another significant innovator with respect to clothing for human motion capture is Thalmic Labs (North). Their work includes patent application publication 20140240223 (Lake et al., Aug. 28, 2014, "Method and Apparatus for Analyzing Capacitive EMG and IMU Sensor Signals for Gesture Control") which discloses a muscle interface device to control connected devices. U.S. patent application publication 20140240103 (Lake et al., Aug. 28, 2014, "Methods and Devices for Combining Muscle Activity Sensor Signals and Inertial Sensor Signals for Gesture-Based Control") discloses a wearable electronic EMG device for use with controllable connected devices.

Another significant innovator with respect to clothing for human motion capture is Bend Labs. Their work includes U.S. Pat. No. 9,874,431 (Reese, Jan. 23, 2018, "Angular Displacement Sensor of Compliant Material"), and U.S. patent application publications 20160033255 (Reese, Feb. 4, 2016, "Angular Displacement Sensor of Compliant Material") and 20170074637 (Reese, Mar. 16, 2017, "Angular Displacement Sensor of Compliant Material") which disclose multi-directional capacitive sensors. U.S. Pat. No. 9,612,102 (Reese et al., Apr. 4, 2017, "Compliant Multi-Region Angular Displacement and Strain Sensors"), and U.S. patent application publications 20160305759 (Reese et al., Oct. 20, 2016, "Compliant Multi-Region Angular Displacement and Strain Sensors") and 20170168567 (Reese et al., Jun. 15, 2017, "Compliant Multi-Region Angular Displacement and Strain Sensors") disclose angular displacement sensors and strain sensors multiple motion sensing regions.

Another significant innovator with respect to clothing for human motion capture is Harvard University. Their work includes U.S. Pat. No. 10,527,507 (Wood et al., Jan. 7, 2020, "Artificial Skin and Elastic Strain Sensor") and U.S. Pat. No. 9,797,791 (Vogt et al., Oct. 24, 2017, "Multi-Axis Force Sensing Soft Artificial Skin"), and U.S. patent application publication 20140238153 (Wood et al., Aug. 28, 2014, "Artificial Skin and Elastic Strain Sensor"), which disclose an elastic strain sensor with conductive fluid.

Another significant innovator with respect to clothing for human motion capture is CTRL-Labs. Their work includes patent application publication 20190228330 (Kaifosh et al., Jul. 25, 2019, "Handstate Reconstruction Based on Multiple Inputs") which discloses methods and systems for recognizing gestures using a plurality of neuromuscular sensors. U.S. Pat. No. 10,429,928 (Morun et al., Oct. 1, 2019, "Systems, Articles, and Methods for Capacitive Electromyography Sensors") and U.S. Pat. No. 10,362,958 (Morun et al., Jul. 30, 2019, "Systems, Articles, and Methods for Electromyography Sensors") disclose EMG sensors which coated with protective barriers and adapted to resistively couple to a user's skin.

Another significant innovator with respect to clothing for human motion capture is IBM. Their work includes U.S. Pat No. 7,771,318 (Narayanaswami, Aug. 10, 2010, "Device for Monitoring a User's Posture") and U.S. Pat. No. 7,850,574 (Narayanaswami, Dec. 14, 2010, "Device for Monitoring a User's Posture") which disclose a wearable device which monitors a person's posture. U.S. patent application publication 20190117157 (Hu et al., Apr. 25, 2019, "Sensors Facilitating Monitoring of Living Entities") discloses methods of manufacturing optical strain sensors.

Another significant innovator with respect to clothing for human motion capture is Apple. Their work includes U.S. Pat. No. 10,488,936 (Baranski et al., Nov. 26, 2019, "Motion and Gesture Input from a Wearable Device"), and U.S. patent application publications 20160091980 (Baranski et al., Mar. 31, 2016, "Motion and Gesture Input from a Wearable Device") and 20190220099 (Baranski et al., Jul. 18, 2019, "Motion and Gesture Input from a Wearable Device") which disclose wearable devices with optical or EMG sensors that recognize gestures of a user's hand, arm, wrist, and fingers. U.S. patent application publication 20190310713 (Wang et al., Oct. 10, 2019, "Sensors for Electronic Finger Devices") discloses finger-mounted devices with strain sensors and/or ultrasonic sensors to measure finger movement.

Another significant innovator with respect to clothing for human motion capture is J-MEX. Their work includes U.S. Pat. No. 10,172,541 (Liao et al., Jan. 8, 2019, "Motion Recognition Device and Method") and U.S. patent application publication 20170086711 (Liao et al., Mar. 30, 2017, "Motion Recognition Device and Method") which disclose a motion recognition device with a first sense signal portion and a second sense signal portion different from the first sense signal portion.

Another significant innovator with respect to clothing for human motion capture is the University of Minnesota. Their work includes U.S. Pat. No. 9,322,121 (Dunne et al., Apr. 26, 2016, "Stitched Stretch Sensor"), U.S. Pat. No. 9,885,621 (Dunne et al., Feb. 6, 2018, "Stitched Stretch Sensor"), and U.S. Pat. No. 10,274,384 (Dunne et al., Apr. 30, 2019, "Stitched Stretch Sensor"), and U.S. patent application publication 20140238151 (Dunne et al., Aug. 28, 2014, "Stitched Stretch Sensor") which disclose a stitched sensor including a conductive thread, and the stitch geometry is configured such that an electrical property of the stitched sensor changes based on at least one of stretching, relaxation, or bending of the textile.

Another significant innovator with respect to clothing for human motion capture is Xenoma. Their work includes patent application publication 20190364983 (Nakajima et al., Dec. 5, 2019, "Wearable Device and Paper Pattern") which discloses a wearable device with sensors, at least one of which is on the front side and the back side respectively.

Another significant innovator with respect to clothing for human motion capture is Facebook. Their work includes U.S. Pat. No. 10,197,459 (Keller et al., Feb. 5, 2019, "Indexable Strain Sensor") which discloses a deformation sensing apparatus comprising an elastic substrate, a conductive element, and an additional conductive element. U.S. Pat. No. 10,502,643 (Keller et al., Dec. 10, 2019, "Resistive-Capacitive Deformation Sensor") and U.S. Pat. No. 10,067,007 (Keller et al., Sep. 4, 2018, "Resistive-Capacitive Deformation Sensor") disclose a deformation sensing apparatus which senses stain in two directions. U.S. Pat. No. 9,816,799 (Keller et al., Nov. 14, 2017, "Embroidered Strain Sensing Elements") discloses a deformation sensing fabric comprising a fabric substrate with a first fabric layer and a first conductive element woven into the first fabric layer.

Another significant innovator with respect to clothing for human motion capture is Footfalls and Heartbeats. Their work includes U.S. Pat. No. 10,119,208 (McMaster, Nov. 6, 2018, "Method for Making Electrically Conductive Textiles and Textile Sensor") which discloses a method for making a textile sensor which includes selecting yarn variables, stitch variables, and/or textile variables. U.S. Pat. No. 10,240,265 (McMaster, Mar. 26, 2019, "Method for Optimizing Contact Resistance in Electrically Conductive Textiles") discloses a method for optimizing contact resistance in electrically conductive yarns and textiles.

Another significant innovator with respect to clothing for human motion capture is Nextiles. Their work includes U.S. Pat. No. 10,458,866 (Sun, Oct. 29, 2019, "Methods of Manufacturing Devices for Static and Dynamic Body Measurements") which discloses a method of fabricating a sensor for static and dynamic body measurements. U.S. Pat. No. 10,378,975 (Sun, Aug. 13, 2019, "Systems, Methods, and Devices for Static and Dynamic Body Measurements")

discloses systems and methods to measure static and dynamic forces of a body using sensors.

Other relevant art with respect to clothing for human motion capture includes the following. U.S. Pat. No. 9,850,600 (Gal, Dec. 26, 2017, "Sensor Garment and Methods of Making the Same") discloses IP sensor conductors with waveforms having legs that are substantially parallel throughout the operating range of stretch. U.S. Pat. No. 6,487,906 (Hock, Dec. 3, 2002, "Flexible Film Sensor System for Monitoring Body Motion") discloses a sequence of low force, high compliance, long extension, piezofilm-based sensors for a biofeedback system for self-monitoring of selected body motions. U.S. patent application publication 20170265810 (Van De Vyver, Sep. 21, 2017, "Elastic Sensor") discloses a stretchable sensor patch comprising an elastic film layer with a stretchability of at least 100% and at least one elastic DEAP strip.

U.S. patent application publication 20190046114 (Bogdanovich et al., Feb. 14, 2019, "Garment System Providing Biometric Monitoring") discloses a garment for monitoring biometric properties of the wearer. U.S. patent application publication 20200008715 (Schroeck et al., Jan. 9, 2020, "Rotation Monitoring System and Method") discloses a rotation monitoring system attached to a limb to identify ranges of motion associated with injuries or poor performance. U.S. patent application publication 20160287175 (Coleman et al., Oct. 6, 2016, "Sensitive, High-Strain, High-Rate, Bodily Motion Sensors Based on Conductive Nano-Material-Rubber Composites") discloses a process for producing conductive composites. U.S. patent application publication 20190185672 (Boland et al., Jun. 20, 2019, "Viscoelastic Conductive Nanomaterial-Polymer Nanocomposites and Sensing Devices Comprising the Composite Material") discloses a homogenous composite material with high strength.

U.S. Pat. No. 8,291,779 (Helmer et al., Oct. 23, 2012, "System and Garment for Detecting Movement") discloses a system for detecting movement of a limb or section of a limb. U.S. patent application publication 20150359455 (Hahami et al., Dec. 17, 2015, "Fiber Optic Shape Sensing Applications") discloses a fiber optic cable and interrogation circuitry. U.S. Pat. No. 8,348,865 (Jeong et al., Jan. 8, 2013, "Non-Intrusive Movement Measuring Apparatus and Method Using Wearable Electro-Conductive Fiber") discloses a non-intrusive movement measuring apparatus and method using wearable electro-conductive fibers. U.S. patent application publication 20170171965 (Youn et al., Jun. 15, 2017, "Stretchable Electronic Device and Method of Fabricating the Same") discloses a stretchable electronic device including a flexible substrate, a conductive fiber pattern formed on the flexible substrate, wherein the conductive fiber pattern has a repetitive circular structure.

U.S. patent application publication 20190342993 (Ahn et al., Nov. 7, 2019, "Stretchable Electronics and Method for Fabricating the Same") discloses stretchable electronics including a stretchable substrate, support patterns disposed on a surface of the stretchable substrate, and output devices disposed on the patterns. U.S. Pat. No. 10,065,074 (Hoang et al., Sep. 4, 2018~T=Training Systems with Wearable Sensors for Providing Users with Feedback") discloses a training system based on mobile technology and the kinematics of human motion which characterizes, analyzes, and supplies feedback to a user based on the user's movements. U.S. patent application publication 20120188158 (Tan et al., Jul. 26, 2012, "Wearable Electromyography-Based Human-Computer Interface") discloses a plurality of Electromyography (EMG) sensors comprising a human-computer interface (HCI) for interacting with computing systems.

U.S. Pat. No. 7,981,057 (Stewart, Jul. 19, 2011, "Joint Motion Sensing to Make a Determination of a Positional Change of an Individual") and U.S. Pat. No. 9,700,238 (Stewart, Jul. 11, 2017, "Joint Motion Sensing to Make a Determination of a Positional Change of an Individual") disclose one or more sensors that produce one or more signals based on one or more joint motions of an individual. U.S. Pat. No. 8,162,857 (Lanfermann et al., Apr. 24, 2012, "Limb Movement Monitoring System") and U.S. patent application publication 20100036288 (Lanfermann et al., Feb. 11, 2010, "Limb Movement Monitoring System") disclose a garment comprising spatially addressable photonic textiles. U.S. patent application publication 20190145752 (Zhu et al., May 16, 2019, "Highly Stretchable Strain Sensor for Human Motion Monitoring") discloses a method to assemble a highly stretchable and highly sensitive strain sensor.

U.S. patent application publication 20170347721 (Greenspan et al., Dec. 7, 2017, "Conductive Thread Stitched Stretch Sensor") discloses conductive thread stitched stretch sensors. U.S. patent application publication 20190390985 (Kwok et al., Dec. 26, 2019, "Real-Time Surface Shape Sensing for Flexible Structures") discloses a surface shape sensor in the form of a flexible and stretchable elastomeric substrate with strain/displacement sensing elements embedded in it. U.S. patent application publication 20190290198 (Belson et al., Sep. 26, 2019, "Systems and Methods for Monitoring Physical Therapy of the Knee and Other Joints") discloses systems, devices, and methods for post-surgical joint range of motion measurement, activity monitoring, as well as monitoring compliance.

SUMMARY OF THE INVENTION

This invention is smart clothing which enables human motion capture through combined analysis of data from multiple types of motion sensors including inertial sensors, strain (or bend) sensors, and electromyographic (EMG) sensor(s). These different types of motion sensors have complementary strengths and weaknesses. For example, inertial motion sensors do not require form-fitting clothing to measure motion and can measure relatively small motions. However, inertial motion sensors can suffer from drift and lack of posture identification when first activated. Strain sensors can help to correct drift and can provide posture identification when first activated, but can be less accurate in loose-fitting clothing and for small motions. Electromyographic (EMG) sensors can provide information about muscle exertion and force that neither inertial sensors nor strain sensors can provide, but require close contact with a person's body. Combining data from all of three of these motion sensor types enables more accurate measurement of human motion through smart clothing.

In an example, this invention can be embodied in smart clothing (e.g. a smart shirt), wherein a portion (e.g. a sleeve) of the clothing has a longitudinal axis which spans a body joint (e.g. an elbow), a first cross-sectional circumference of the portion is proximal relative to the body joint (e.g. around the upper arm), and a second cross-sectional circumference is distal relative to the body joint (e.g. around the lower arm). As used herein, proximal means closer to a person's heart and distal means farther from the person's heart when the person is in Vitruvian Man configuration (made famous by Leonardo da Vinci and also shown in FIG. 1). Also, a first inertial motion sensor (e.g. an accelerometer and gyroscope)

is incorporated into the clothing at the first cross-sectional circumference and a second inertial motion sensor is incorporated into the smart clothing at the second cross-sectional circumference. Further, two strain (or bend) sensors in the smart clothing span the body joint between the first cross-sectional circumference and the second cross-sectional circumference. These strain sensors collect data concerning transmission of electromagnetic energy through them, which is changed by motion of the body joint. Several examples of strain sensor configurations are disclosed herein. Further, an electromyographic (EMG) sensor is incorporated into the smart clothing and collects data concerning electromagnetic energy emitted by muscles and/or nerves. This invention also includes a data processor which analyzes data from the inertial motion sensors, the strain sensors, and the electromyographic (EMG) sensor to measure the configuration and/or motion of the body joint.

INTRODUCTION TO THE FIGURES

FIG. 1 shows a smart shirt with two inertial sensors, two strain (or bend) sensors, and an electromyographic (EMG) sensor.

DETAILED DESCRIPTION OF THE FIGURES

FIG. 1 shows an example of a device or system for capturing human motion comprising: an article of clothing 103 worn by a person 101, wherein a portion 104 of the article of clothing has a longitudinal axis which is configured to span a body joint 102, wherein the portion has a first cross-sectional circumference 105 which is proximal relative to the body joint, wherein the portion has a second cross-sectional circumference 106 which is distal relative to the body joint, and wherein proximal means closer to and distal means farther from the person's heart when the person is in Vitruvian Man configuration (shown in FIG. 1); a first inertial motion sensor 107 which is incorporated into the portion at the first cross-sectional circumference; a second inertial motion sensor 108 which is incorporated into the portion at the second cross-sectional circumference; a first strain sensor 109 which is incorporated into the portion and spans the body joint between the first cross-sectional circumference and the second cross-sectional circumference, wherein the first strain sensor collects data concerning the transmission of electromagnetic energy through the first strain sensor; a second strain sensor 110 which is incorporated into the portion and spans the body joint between the first cross-sectional circumference and the second cross-sectional circumference, wherein the second strain sensor collects data concerning the transmission of electromagnetic energy through the second strain sensor; an electromyographic sensor 111 which is incorporated into the portion and is in electromagnetic communication with a muscle which moves the body joint and/or with nerves which innervate the muscle, and wherein the electromyographic sensor collects data concerning electromagnetic energy emitted by the muscle and/or the nerves; and a data processor 112 which analyzes data from the first inertial motion sensor, the second inertial motion sensor, the first strain sensor, the second strain sensor, and the electromyographic sensor to measure a configuration and/or motion of the body joint.

In the example shown in FIG. 1: the article of clothing is a shirt, the portion is a sleeve, the body joint is an elbow, the first cross-sectional circumference is around the person's upper arm, the second cross-sectional circumference is around the person's lower arm, and the data processor is worn by the person. In another example, the data processor can be at a remote location with which the wearable components are in electromagnetic communication.

In an example, a device or system for capturing human motion can comprise: an article of clothing worn by a person, wherein a portion of the article of clothing has a longitudinal axis which is configured to span a body joint, wherein the portion has a first cross-sectional circumference which is proximal relative to the body joint, wherein the portion has a second cross-sectional circumference which is distal relative to the body joint, and wherein proximal means closer to and distal means farther from the person's heart when the person is in Vitruvian Man configuration; a first inertial motion sensor which is incorporated into the portion at the first cross-sectional circumference; a second inertial motion sensor which is incorporated into the portion at the second cross-sectional circumference; a first strain sensor which is incorporated into the portion and spans the body joint between the first cross-sectional circumference and the second cross-sectional circumference, wherein the first strain sensor collects data concerning the transmission of electromagnetic energy through the first strain sensor; a second strain sensor which is incorporated into the portion and spans the body joint between the first cross-sectional circumference and the second cross-sectional circumference, wherein the second strain sensor collects data concerning the transmission of electromagnetic energy through the second strain sensor; an electromyographic sensor which is incorporated into the portion and is in electromagnetic communication with a muscle which moves the body joint and/or with nerves which innervate the muscle, and wherein the electromyographic sensor collects data concerning electromagnetic energy emitted by the muscle and/or the nerves; and a data processor which analyzes data from the first inertial motion sensor, the second inertial motion sensor, the first strain sensor, the second strain sensor, and the electromyographic sensor to measure a configuration and/or motion of the body joint.

In an example, a device or system for capturing human motion can comprise: an article of clothing worn by a person, wherein a portion of the article of clothing has a longitudinal axis which is configured to span a body joint, wherein the portion has a first cross-sectional circumference which is proximal relative to the body joint, wherein the portion has a second cross-sectional circumference which is distal relative to the body joint, and wherein proximal means closer to and distal means farther from the person's heart when the person is in Vitruvian Man configuration; a first inertial motion sensor which is incorporated into the portion at the first cross-sectional circumference; a second inertial motion sensor which is incorporated into the portion at the second cross-sectional circumference; a first strain sensor which is incorporated into the portion and spans the body joint at a first angle relative to the longitudinal axis, wherein the first strain sensor collects data concerning the transmission of electromagnetic energy through the first strain sensor; a second strain sensor which is incorporated into the portion and spans the body joint at a second angle relative to the longitudinal axis, wherein the second angle is rotated between 10 and 50 degrees relative to the first angle, and wherein the second strain sensor collects data concerning the transmission of electromagnetic energy through the second strain sensor; an electromyographic sensor which is incorporated into the portion and is in electromagnetic communication with a muscle which moves the body joint and/or with nerves which innervate the muscle, and wherein the electromyographic sensor collects data concerning electromagnetic energy emitted by the muscle and/or the nerves; and a data processor which analyzes data from the first inertial motion sensor, the second inertial motion sensor, the first strain sensor, the second strain sensor, and the electromyographic sensor to measure a configuration and/or motion of the body joint.

In an example, a device or system for capturing human motion can comprise: an article of clothing worn by a person, wherein a portion of the article of clothing has a longitudinal axis which is configured to span a body joint, wherein the portion has a first cross-sectional circumference which is proximal relative to the body joint, wherein the portion has a second cross-sectional circumference which is distal relative to the body joint, and wherein proximal means closer to and distal means farther from the person's heart when the person is in Vitruvian Man configuration; a first inertial motion sensor which is incorporated into the portion at the first cross-sectional circumference; a second inertial motion sensor which is incorporated into the portion at the second cross-sectional circumference; a first strain sensor made with an elastomeric silicone-based polymer which has been doped, impregnated, or coated with electroconductive material and is incorporated into the portion and spans the body joint between the first cross-sectional circumference and the second cross-sectional circumference, wherein the first strain sensor collects data concerning the transmission of electromagnetic energy through the first strain sensor; a second strain sensor made with an elastomeric silicone-based polymer which has been doped, impregnated, or coated with electroconductive material and is incorporated into the portion and spans the body joint between the first cross-sectional circumference and the second cross-sectional circumference, wherein the second strain sensor collects data concerning the transmission of electromagnetic energy through the second strain sensor; an electromyographic sensor which is incorporated into the portion and is in electromagnetic communication with a muscle which moves the body joint and/or with nerves which innervate the muscle, and wherein the electromyographic sensor collects data concerning electromagnetic energy emitted by the muscle and/or the nerves; and a data processor which analyzes data from the first inertial motion sensor, the second inertial motion sensor, the first strain sensor, the second strain sensor, and the electromyographic sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is incorporated into (or attached to) the portion and spans the body joint between the first cross-sectional circumference and the second cross-sectional circumference, and wherein the first strain sensor collects data concerning the transmission of energy through the first strain sensor; (e) a second strain (and/or bend) sensor which is incorporated into (or attached to) the portion and spans the body joint between the first cross-sectional circumference and the second cross-sectional circumference, and wherein the second strain sensor collects data concerning the transmission of energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a strain (and/or bend) sensor which is incorporated into (or attached to) the portion and spans the body joint between the first cross-sectional circumference and the second cross-sectional circumference, and wherein the strain sensor collects data concerning the transmission of energy through the strain sensor; (e) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (f) a data processor which analyzes data from the first inertial motion sensor, the second inertial motion sensor, the strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is incorporated into (or attached to) the portion and spans the body joint between the first cross-sectional circumference and the second cross-sectional circumference, and wherein the first strain sensor collects data concerning the transmission of energy through the first strain sensor; (e) a second strain (and/or bend) sensor which is incorporated into (or attached to) the portion and spans the body joint between the first cross-sectional circumference and the second cross-sectional circumference, and wherein the second strain sensor collects data concerning the transmission of energy through the second strain sensor; and (f) a data processor which analyzes data from the first inertial motion sensor, the second inertial motion sensor, the first strain sensor, and the second strain sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor comprising an accelerometer and a gyroscope which is incorporated into (or attached to) the portion at the first cross-sectional circumference; (c) a second inertial motion sensor comprising an accelerometer and a gyroscope which is incorporated into (or attached to) the portion at the second cross-sectional circumference; (d) a first strain (and/or bend) sensor which is incorporated into (or attached to) the portion and spans the body joint between the first cross-sectional circumference and the second cross-sectional circumference, wherein the first strain sensor collects data concerning the transmission of electromagnetic energy through the first strain sensor; (e) a second strain (and/or bend) sensor which is incorporated into (or attached to) the portion and spans the body joint between the first cross-sectional circumference and the second cross-sectional circumference, wherein the second strain sensor collects data concerning the transmission of electromagnetic energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor comprising an accelerometer which is incorporated into (or attached to) the portion at the first cross-sectional circumference; (c) a second inertial motion sensor comprising an accelerometer which is incorporated into (or attached to) the portion at the second cross-sectional circumference; (d) a first strain (and/or bend) sensor which is incorporated into (or attached to) the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor which is incorporated into (or attached to) the portion and spans the body joint between the first cross-sectional circumference and the second cross-sectional circumference, and wherein the second strain sensor collects data concerning the transmission of electromagnetic energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first (partial) helical capacitive strain (and/or bend) sensor which is incorporated into (or attached to) the portion and spans the body joint between the first cross-sectional circumference and the second cross-sectional circumference, and wherein the first strain sensor collects data concerning the transmission of energy through the first strain sensor; (e) a second (partial) helical capacitive strain (and/or bend) sensor which is incorporated into (or attached to) the portion and spans the body joint between the first cross-sectional circumference and the second cross-sectional circumference, and wherein the second strain sensor collects data concerning the transmission of energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first circular and/or annular strain (and/or bend) sensor which is incorporated into (or attached to) the portion and spans the body joint between the first cross-sectional circumference and the second cross-sectional circumference, and wherein the first strain sensor collects data concerning the transmission of energy through the first strain sensor; (e) a second circular and/or annular strain (and/or bend) sensor which is incorporated into (or attached to) the portion and spans the body joint between the first cross-sectional circumference and the second cross-sectional circumference, and wherein the second strain sensor collects data concerning the transmission of energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first dielectric elastomer strain (and/or bend) sensor which is incorporated into (or attached to) the portion and spans the body joint between the first cross-sectional circumference and the second cross-sectional circumference, and wherein the first strain sensor collects data concerning the transmission of energy through the first strain sensor; (e) a second dielectric elastomer strain (and/or bend) sensor which is incorporated into (or attached to) the portion and spans the body joint between the first cross-sectional circumference and the second cross-sectional circumference, and wherein the second strain sensor collects data concerning the transmission of energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first helical strain (and/or bend) sensor which is incorporated into (or attached to) the portion and spans the body joint between the first cross-sectional circumference and the second cross-sectional circumference, and wherein the first strain sensor collects data concerning the transmission of energy through the first strain sensor; (e) a second helical strain (and/or bend) sensor which is incorporated into (or attached to) the portion and spans the body joint between the first cross-sectional circumference and the second cross-sectional circumference, and wherein the second strain sensor collects data concerning the transmission of energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first optical strain (and/or bend) sensor made from PMMA or a styrene-based polymer which is incorporated into (or attached to) the portion and spans the body joint between the first cross-sectional circumference and the second cross-sectional circumference, and wherein the first optical strain sensor collects data concerning the transmission of light energy through the first optical strain sensor; (e) a second optical strain (and/or bend) sensor made from PMMA or a styrene-based polymer which is incorporated into (or attached to) the portion and spans the body joint between the first cross-sectional circumference and the second cross-sectional circumference, and wherein the second optical strain sensor collects data concerning the transmission of light energy through the second optical strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first piezoresistive strain (and/or bend) sensor which is incorporated into (or attached to) the portion and spans the body joint between the first cross-sectional circumference and the second cross-sectional circumference, and wherein the first strain sensor collects data concerning the transmission of energy through the first strain sensor; (e) a second piezoresistive strain (and/or bend) sensor which is incorporated into (or attached to) the portion and spans the body joint between the first cross-sectional circumference and the second cross-sectional circumference, and wherein the second strain sensor collects data concerning the transmission of energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor comprising a conductive pathway which is generally parallel to the longitudinal axis of the portion which is incorporated into (or attached to) the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor comprising a conductive pathway which is generally parallel to the longitudinal axis of the portion which is incorporated into (or attached to) the portion and spans the body joint between the first cross-sectional circumference and the second cross-sectional circumference, and wherein the second strain sensor collects data concerning the transmission of electromagnetic energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor comprising a conductive pathway which is generally parallel to the longitudinal axis of the portion which is incorporated into (or attached to) the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor comprising a conductive pathway which is generally perpendicular to the longitudinal axis of the portion which is incorporated into (or attached to) the portion and spans the body joint between the first cross-sectional circumference and the second cross-sectional circumference, and wherein the second strain sensor collects data concerning the transmission of electromagnetic energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor comprising a conductive pathway which is generally parallel to the longitudinal axis of the portion which is incorporated into (or attached to) the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor comprising a conductive pathway which intersects the longitudinal axis of the portion at an acute angle which is incorporated into (or attached to) the portion and spans the body joint between the first cross-sectional circumference and the second cross-sectional circumference, and wherein the second strain sensor collects data concerning the transmission of electromagnetic energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor comprising a first capacitor in a first layer of the portion which spans the body joint between the first cross-sectional circumference and the second cross-sectional circumference, and wherein the first strain sensor collects data concerning the transmission of energy through the first strain sensor; (e) a second strain (and/or bend) sensor comprising a first capacitor in a first layer of the portion which spans the body joint between the first cross-sectional circumference and the second cross-sectional circumference, and wherein the second strain sensor collects data concerning the transmission of energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor comprising a light energy transmission sensor which is incorporated into (or attached to) the portion and spans the body joint between the first cross-sectional circumference and the second cross-sectional circumference, and wherein the first strain sensor collects data concerning the transmission of light energy through the first strain sensor; (e) a second strain (and/or bend) sensor comprising a light energy transmission sensor which is incorporated into (or attached to) the portion and spans the body joint between the first cross-sectional circumference and the second cross-sectional circumference, and wherein the second strain sensor collects data concerning the transmission of light energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor comprising a light energy transmission sensor made from an elastomeric polymer doped with dye which is incorporated into (or attached to) the portion and spans the body joint between the first cross-sectional circumference and the second cross-sectional circumference, and wherein the first strain sensor collects data concerning the transmission of light energy through the first strain sensor; (e) a second strain (and/or bend) sensor comprising a light energy transmission sensor made from an elastomeric polymer doped with dye which is incorporated into (or attached to) the portion and spans the body joint between the first cross-sectional circumference and the second cross-sectional circumference, and wherein the second strain sensor collects data concerning the transmission of light energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor comprising a light-transmitting optical fiber which is incorporated into (or attached to) the portion and spans the body joint between the first cross-sectional circumference and the second cross-sectional circumference, and wherein the first strain sensor collects data concerning the transmission of light energy through the first strain sensor; (e) a second strain (and/or bend) sensor comprising a light-transmitting optical fiber which is incorporated into (or attached to) the portion and spans the body joint between the first cross-sectional circumference and the second cross-sectional circumference, and wherein the second strain sensor collects data concerning the transmission of light energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor comprising a first capacitor which is incorporated into (or attached to) the portion and spans the body joint between the first cross-sectional circumference and the second cross-sectional circumference, and wherein the first strain sensor collects data concerning the transmission of energy through the first strain sensor; (e) a second strain (and/or bend) sensor comprising a second capacitor which is incorporated into (or attached to) the portion and spans the body joint between the first cross-sectional circumference and the second cross-sectional circumference, wherein a longitudinal orientation of the second capacitor is orthogonal to a longitudinal orientation of the first capacitor, and wherein the second strain sensor collects data concerning the transmission of energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor comprising a series of loops which is stitched into the portion and spans the body joint between the first cross-sectional circumference and the second cross-sectional circumference, and wherein the first strain sensor collects data concerning the transmission of energy through the first strain sensor; (e) a second strain (and/or bend) sensor comprising a series of loops which is stitched into the portion and spans the body joint between the first cross-sectional circumference and the second cross-sectional circumference, and wherein the second strain sensor collects data concerning the transmission of energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor comprising alternating high-conductivity and low-conductivity flexible layers, wherein this first strain sensor is incorporated into (or attached to) the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor comprising alternating high-conductivity and low-conductivity flexible layers, wherein this second strain sensor is incorporated into (or attached to) the portion and spans the body joint between the first cross-sectional circumference and the second cross-sectional circumference, and wherein the second strain sensor collects data concerning the transmission of electromagnetic energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is incorporated into (or attached to) the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor comprising alternating layers of ladyfingers dipped in coffee and a whipped mixture of eggs, sugar, and mascarpone cheese flavored with cocoa; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor comprising an electroconductive fluid in a flexible channel which is incorporated into (or attached to) the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor comprising an electroconductive fluid in a flexible channel which is incorporated into (or attached to) the portion and spans the body joint between the first cross-sectional circumference and the second cross-sectional circumference, and wherein the second strain sensor collects data concerning the transmission of electromagnetic energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor comprising an electromagnetic energy conductivity sensor which is incorporated into (or attached to) the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor comprising an electromagnetic energy conductivity sensor which is incorporated into (or attached to) the portion and spans the body joint between the first cross-sectional circumference and the second cross-sectional circumference, and wherein the second strain sensor collects data concerning the transmission of electromagnetic energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor comprising an electromagnetic energy resistance sensor which is incorporated into (or attached to) the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor comprising an electromagnetic energy resistance sensor which is incorporated into (or attached to) the portion and spans the body joint between the first cross-sectional circumference and the second cross-sectional circumference, and wherein the second strain sensor collects data concerning the transmission of electromagnetic energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor comprising an electromagnetic energy impedance sensor which is incorporated into (or attached to) the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor comprising an electromagnetic energy impedance sensor which is incorporated into (or attached to) the portion and spans the body joint between the first cross-sectional circumference and the second cross-sectional circumference, and wherein the second strain sensor collects data concerning the transmission of electromagnetic energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor comprising an electromagnetic energy capacitance sensor which is incorporated into (or attached to) the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor comprising an electromagnetic energy capacitance sensor which is incorporated into (or attached to) the portion and spans the body joint between the first cross-sectional circumference and the second cross-sectional circumference, and wherein the second strain sensor collects data concerning the transmission of electromagnetic energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor comprising fluid in a flexible microchannel which is incorporated into (or attached to) the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor comprising fluid in a flexible microchannel which is incorporated into (or attached to) the portion and spans the body joint between the first cross-sectional circumference and the second cross-sectional circumference, and wherein the second strain sensor collects data concerning the transmission of electromagnetic energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor comprising fluid in a flexible microchannel which is incorporated into (or attached to) the portion and spans the body joint between the first cross-sectional circumference and the second cross-sectional circumference, and wherein the first strain sensor collects data concerning the pressure of the fluid in the first strain sensor; (e) a second strain (and/or bend) sensor comprising fluid in a flexible microchannel which is incorporated into (or attached to) the portion and spans the body joint between the first cross-sectional circumference and the second cross-sectional circumference, and wherein the second strain sensor collects data concerning a pressure of the fluid in the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor comprising two high-conductivity flexible layers separated by a low-conductivity flexible layer, wherein this first strain sensor is incorporated into (or attached to) the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor comprising two high-conductivity flexible layers separated by a low-conductivity flexible layer, wherein this second strain sensor is incorporated into (or attached to) the portion and spans the body joint between the first cross-sectional circumference and the second cross-sectional circumference, and wherein the second strain sensor collects data concerning the transmission of electromagnetic energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor comprising two high-conductivity flexible layers separated by a space or gap, wherein this first strain sensor is incorporated into (or attached to) the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor comprising two high-conductivity flexible layers separated by a space or gap, wherein this second strain sensor is incorporated into (or attached to) the portion and spans the body joint between the first cross-sectional circumference and the second cross-sectional circumference, and wherein the second strain sensor collects data concerning the transmission of electromagnetic energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor made by printing conductive silicone-based ink onto portion which spans the body joint between the first cross-sectional circumference and the second cross-sectional circumference, and wherein the first strain sensor collects data concerning the transmission of energy through the first strain sensor; (e) a second strain (and/or bend) sensor made by printing conductive silicone-based ink onto portion which spans the body joint between the first cross-sectional circumference and the second cross-sectional circumference, and wherein the second strain sensor collects data concerning the transmission of energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor made from a silicone polymer which has been embedded, impregnated, doped, or coated with conductive material which is incorporated into (or attached to) the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor made from a silicone polymer which has been embedded, impregnated, doped, or coated with conductive material which is incorporated into (or attached to) the portion and spans the body joint between the first cross-sectional circumference and the second cross-sectional circumference, and wherein the second strain sensor collects data concerning the transmission of electromagnetic energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor made from a silicone polymer which has been embedded, impregnated, doped, or coated with silver particles which is incorporated into (or attached to) the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor made from a silicone polymer which has been embedded, impregnated, doped, or coated with silver particles which is incorporated into (or attached to) the portion and spans the body joint between the first cross-sectional circumference and the second cross-sectional circumference, and wherein the second strain sensor collects data concerning the transmission of electromagnetic energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor made from a silicone polymer which has been embedded, impregnated, doped, or coated with carbon which is incorporated into (or attached to) the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor made from a silicone polymer which has been embedded, impregnated, doped, or coated with carbon which is incorporated into (or attached to) the portion and spans the body joint between the first cross-sectional circumference and the second cross-sectional circumference, and wherein the second strain sensor collects data concerning the transmission of electromagnetic energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor made from an elastomeric polymer impregnated, doped, or coated with carbon black which is incorporated into (or attached to) the portion and spans the body joint between the first cross-sectional circumference and the second cross-sectional circumference, and wherein the first strain sensor collects data concerning the transmission of energy through the first strain sensor; (e) a second strain (and/or bend) sensor made from an elastomeric polymer impregnated, doped, or coated with carbon black which is incorporated into (or attached to) the portion and spans the body joint between the first cross-sectional circumference and the second cross-sectional circumference, and wherein the second strain sensor collects data concerning the transmission of energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor made from an elastomeric polymer impregnated, doped, or coated with graphene which is incorporated into (or attached to) the portion and spans the body joint between the first cross-sectional circumference and the second cross-sectional circumference, and wherein the first strain sensor collects data concerning the transmission of energy through the first strain sensor; (e) a second strain (and/or bend) sensor made from an elastomeric polymer impregnated, doped, or coated with graphene which is incorporated into (or attached to) the portion and spans the body joint between the first cross-sectional circumference and the second cross-sectional circumference, and wherein the second strain sensor collects data concerning the transmission of energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor made from an elastomeric polymer impregnated, doped, or coated with iron particles which is incorporated into (or attached to) the portion and spans the body joint between the first cross-sectional circumference and the second cross-sectional circumference, and wherein the first strain sensor collects data concerning the transmission of energy through the first strain sensor; (e) a second strain (and/or bend) sensor made from an elastomeric polymer impregnated, doped, or coated with iron particles which is incorporated into (or attached to) the portion and spans the body joint between the first cross-sectional circumference and the second cross-sectional circumference, and wherein the second strain sensor collects data concerning the transmission of energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor made from an elastomeric polymer impregnated, doped, or coated with carbon nanotubes which is incorporated into (or attached to) the portion and spans the body joint between the first cross-sectional circumference and the second cross-sectional circumference, and wherein the first strain sensor collects data concerning the transmission of energy through the first strain sensor; (e) a second strain (and/or bend) sensor made from an elastomeric polymer impregnated, doped, or coated with carbon nanotubes which is incorporated into (or attached to) the portion and spans the body joint between the first cross-sectional circumference and the second cross-sectional circumference, and wherein the second strain sensor collects data concerning the transmission of energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor made from an elastomeric polymer which has been impregnated, doped, or coated with carbon, copper, silver, nickel, aluminum, steel, or iron and which is incorporated into (or attached to) the portion and spans the body joint between the first cross-sectional circumference and the second cross-sectional circumference, and wherein the first strain sensor collects data concerning the transmission of energy through the first strain sensor; (e) a second strain (and/or bend) sensor made from an elastomeric polymer which has been impregnated, doped, or coated with carbon, copper, silver, nickel, aluminum, steel, or iron and which is incorporated into (or attached to) the portion and spans the body joint between the first cross-sectional circumference and the second cross-sectional circumference, and wherein the second strain sensor collects data concerning the transmission of energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor made from an elastomeric polymer which has been embedded, impregnated, doped, or coated with conductive material which is incorporated into (or attached to) the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor made from an elastomeric polymer which has been embedded, impregnated, doped, or coated with conductive material which is incorporated into (or attached to) the portion and spans the body joint between the first cross-sectional circumference and the second cross-sectional circumference, and wherein the second strain sensor collects data concerning the transmission of electromagnetic energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor made from an polyurethane which has been embedded, impregnated, doped, or coated with silver particles is incorporated into (or attached to) the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor made from an polyurethane which has been embedded, impregnated, doped, or coated with silver particles is incorporated into (or attached to) the portion and spans the body joint between the first cross-sectional circumference and the second cross-sectional circumference, and wherein the second strain sensor collects data concerning the transmission of electromagnetic energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor made from an polyurethane which has been impregnated, doped, or coated with carbon is incorporated into (or attached to) the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor made from an polyurethane which has been embedded, impregnated, doped, or coated with carbon is incorporated into (or attached to) the portion and spans the body joint between the first cross-sectional circumference and the second cross-sectional circumference, and wherein the second strain sensor collects data concerning the transmission of electromagnetic energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor made from hydrogel which is incorporated into (or attached to) the portion and spans the body joint between the first cross-sectional circumference and the second cross-sectional circumference, and wherein the first strain sensor collects data concerning the transmission of energy through the first strain sensor; (e) a second strain (and/or bend) sensor made from hydrogel which is incorporated into (or attached to) the portion and spans the body joint between the first cross-sectional circumference and the second cross-sectional circumference, and wherein the second strain sensor collects data concerning the transmission of energy through the second strain sensor; (f) an EMG (electromyographic) sensor made from hydrogel which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor made from nylon, rubber, or spandex which has been impregnated, doped, or coated with carbon, copper, silver, nickel, aluminum, steel, or iron and which is incorporated into (or attached to) the portion and spans the body joint between the first cross-sectional circumference and the second cross-sectional circumference, and wherein the first strain sensor collects data concerning the transmission of energy through the first strain sensor; (e) a second strain (and/or bend) sensor made from nylon, rubber, or spandex which has been impregnated, doped, or coated with carbon, copper, silver, nickel, aluminum, steel, or iron and which is incorporated into (or attached to) the portion and spans the body joint between the first cross-sectional circumference and the second cross-sectional circumference, and wherein the second strain sensor collects data concerning the transmission of energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor made from polydimethylsiloxane (PDMS) which has been embedded, impregnated, doped, or coated with conductive material which is incorporated into (or attached to) the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor made from polydimethylsiloxane (PDMS) which has been embedded, impregnated, doped, or coated with conductive material which is incorporated into (or attached to) the portion and spans the body joint between the first cross-sectional circumference and the second cross-sectional circumference, and wherein the second strain sensor collects data concerning the transmission of electromagnetic energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor made from polydimethylsiloxane (PDMS) which has been embedded, impregnated, doped, or coated with silver particles which is incorporated into (or attached to) the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor made from polydimethylsiloxane (PDMS) which has been embedded, impregnated, doped, or coated with silver particles which is incorporated into (or attached to) the portion and spans the body joint between the first cross-sectional circumference and the second cross-sectional circumference, and wherein the second strain sensor collects data concerning the transmission of electromagnetic energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor made from polydimethylsiloxane (PDMS) which has been embedded, impregnated, doped, or coated with carbon which is incorporated into (or attached to) the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor made from polydimethylsiloxane (PDMS) which has been embedded, impregnated, doped, or coated with carbon which is incorporated into (or attached to) the portion and spans the body joint between the first cross-sectional circumference and the second cross-sectional circumference, and wherein the second strain sensor collects data concerning the transmission of electromagnetic energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor made from polyurethane which has been embedded, impregnated, doped, or coated with conductive material which is incorporated into (or attached to) the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor made from polyurethane which has been embedded, impregnated, doped, or coated with conductive material which is incorporated into (or attached to) the portion and spans the body joint between the first cross-sectional circumference and the second cross-sectional circumference, and wherein the second strain sensor collects data concerning the transmission of electromagnetic energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor made with conductive ink which is printed onto the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor made with conductive ink which is printed onto the portion and spans the body joint between the first cross-sectional circumference and the second cross-sectional circumference, and wherein the second strain sensor collects data concerning the transmission of electromagnetic energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor made with utadyl, latex, neoprene, or nitrile which is incorporated into (or attached to) the portion and spans the body joint between the first cross-sectional circumference and the second cross-sectional circumference, and wherein the first strain sensor collects data concerning the transmission of energy through the first strain sensor; (e) a second strain (and/or bend) sensor made with utadyl, latex, neoprene, or nitrile which is incorporated into (or attached to) the portion and spans the body joint between the first cross-sectional circumference and the second cross-sectional circumference, and wherein the second strain sensor collects data concerning the transmission of energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor comprising a thermoplastic elastomer which has been doped and/or coated with conductive material and spans the body joint between the first cross-sectional circumference and the second cross-sectional circumference, and wherein the first strain sensor collects data concerning the transmission of electromagnetic energy through the first strain sensor; (e) a second strain (and/or bend) sensor strain (and/or bend) sensor comprising a thermoplastic elastomer which has been doped and/or coated with conductive material and spans the body joint between the first cross-sectional circumference and the second cross-sectional circumference, and wherein the second strain sensor collects data concerning the transmission of electromagnetic energy through the second optical strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor comprising an elastomeric insulating layer between two elastomeric conductive layers which spans the body joint between the first cross-sectional circumference and the second cross-sectional circumference, and wherein the first strain sensor collects data concerning the transmission of electromagnetic energy through the first strain sensor; (e) a second strain (and/or bend) sensor strain (and/or bend) sensor comprising an elastomeric insulating layer between two elastomeric conductive layers which spans the body joint between the first cross-sectional circumference and the second cross-sectional circumference, and wherein the second strain sensor collects data concerning the transmission of electromagnetic energy through the second optical strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor comprising thermoplastic polyurethane (TPU) which has been doped and/or coated with conductive material and spans the body joint between the first cross-sectional circumference and the second cross-sectional circumference, and wherein the first strain sensor collects data concerning the transmission of electromagnetic energy through the first strain sensor; (e) a second strain (and/or bend) sensor strain (and/or bend) sensor comprising thermoplastic polyurethane (TPU) which has been doped and/or coated with conductive material and spans the body joint between the first cross-sectional circumference and the second cross-sectional circumference, and wherein the second strain sensor collects data concerning the transmission of electromagnetic energy through the second optical strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor made from polyimide (PI), polyethylene oxide (PEO), or polyvinylpyrrolidone (PVP) which is incorporated into (or attached to) the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor strain (and/or bend) sensor made from polyimide (PI), polyethylene oxide (PEO), or polyvinylpyrrolidone (PVP) which is incorporated into (or attached to) the portion and spans the body joint between the first cross-sectional circumference and the second cross-sectional circumference, and wherein the second strain sensor collects data concerning the transmission of electromagnetic energy through the second optical strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor made from polystyrene (PS) or polyacrylonitrile (PAN) which is incorporated into (or attached to) the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor strain (and/or bend) sensor made from polystyrene (PS) or polyacrylonitrile (PAN) which is incorporated into (or attached to) the portion and spans the body joint between the first cross-sectional circumference and the second cross-sectional circumference, and wherein the second strain sensor collects data concerning the transmission of electromagnetic energy through the second optical strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor made from polyurethane (PU) which is incorporated into (or attached to) the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor strain (and/or bend) sensor made from polyurethane (PU) which is incorporated into (or attached to) the portion and spans the body joint between the first cross-sectional circumference and the second cross-sectional circumference, and wherein the second strain sensor collects data concerning the transmission of electromagnetic energy through the second optical strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor made from polyvinyl alcohol (PVA) which is incorporated into (or attached to) the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor strain (and/or bend) sensor made from polyvinyl alcohol (PVA) which is incorporated into (or attached to) the portion and spans the body joint between the first cross-sectional circumference and the second cross-sectional circumference, and wherein the second strain sensor collects data concerning the transmission of electromagnetic energy through the second optical strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is made by 3D printing conductive ink onto the portion and which spans the body joint between the first cross-sectional circumference and the second cross-sectional circumference, and wherein the first strain sensor collects data concerning the transmission of electromagnetic energy through the first strain sensor; (e) a second strain (and/or bend) sensor strain (and/or bend) sensor which is made by 3D printing conductive ink onto the portion and which spans the body joint between the first cross-sectional circumference and the second cross-sectional circumference, and wherein the second strain sensor collects data concerning the transmission of electromagnetic energy through the second optical strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is made by 3D printing conductive elastomer ink onto the portion and which spans the body joint between the first cross-sectional circumference and the second cross-sectional circumference, and wherein the first strain sensor collects data concerning the transmission of electromagnetic energy through the first strain sensor; (e) a second strain (and/or bend) sensor strain (and/or bend) sensor which is made by 3D printing conductive elastomer ink onto the portion and which spans the body joint between the first cross-sectional circumference and the second cross-sectional circumference, and wherein the second strain sensor collects data concerning the transmission of electromagnetic energy through the second optical strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is made by jetting conductive ink onto the portion and which spans the body joint between the first cross-sectional circumference and the second cross-sectional circumference, and wherein the first strain sensor collects data concerning the transmission of electromagnetic energy through the first strain sensor; (e) a second strain (and/or bend) sensor strain (and/or bend) sensor which is made by jetting conductive ink onto the portion and which spans the body joint between the first cross-sectional circumference and the second cross-sectional circumference, and wherein the second strain sensor collects data concerning the transmission of electromagnetic energy through the second optical strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is made by screening conductive ink onto the portion and which spans the body joint between the first cross-sectional circumference and the second cross-sectional circumference, and wherein the first strain sensor collects data concerning the transmission of electromagnetic energy through the first strain sensor; (e) a second strain (and/or bend) sensor strain (and/or bend) sensor which is made by screening conductive ink onto the portion and which spans the body joint between the first cross-sectional circumference and the second cross-sectional circumference, and wherein the second strain sensor collects data concerning the transmission of electromagnetic energy through the second optical strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is made by spraying conductive elastomer ink onto the portion and which spans the body joint between the first cross-sectional circumference and the second cross-sectional circumference, and wherein the first strain sensor collects data concerning the transmission of electromagnetic energy through the first strain sensor; (e) a second strain (and/or bend) sensor strain (and/or bend) sensor which is made by spraying conductive elastomer ink onto the portion and which spans the body joint between the first cross-sectional circumference and the second cross-sectional circumference, and wherein the second strain sensor collects data concerning the transmission of electromagnetic energy through the second optical strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is adhered to the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor which is adhered to the portion and spans the body joint between the first cross-sectional circumference and the second cross-sectional circumference, and wherein the second strain sensor collects data concerning the transmission of electromagnetic energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is embroidered onto the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor which is embroidered onto the portion and spans the body joint between the first cross-sectional circumference and the second cross-sectional circumference, and wherein the second strain sensor collects data concerning the transmission of electromagnetic energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) a pair of pants (or shorts) worn by a person, wherein a portion of the pair of pants (or shorts) has a longitudinal axis which spans a hip, wherein the portion has a first cross-sectional circumference which is proximal relative to the hip, wherein the portion has a second cross-sectional circumference which is distal relative to the hip, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is incorporated into (or attached to) the portion and spans the hip between the first cross-sectional circumference and the second cross-sectional circumference, and wherein the first strain sensor collects data concerning the transmission of electromagnetic energy through the first strain sensor; (e) a second strain (and/or bend) sensor which is incorporated into (or attached to) the portion and spans the hip between the first cross-sectional circumference and the second cross-sectional circumference, and wherein the second strain sensor collects data concerning the transmission of electromagnetic energy through the second strain sensor; (f) an EMG (electromyographic) sensor which is incorporated into (or attached to) the portion and is in electromagnetic communication with a muscle which moves the hip and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the hip.

In an example, a device or system for capturing human motion can comprise: (a) a pair of pants worn by a person, wherein a leg of the pair of pants has a longitudinal axis which spans a knee, wherein the leg has a first cross-sectional circumference which is proximal relative to the knee, wherein the leg has a second cross-sectional circumference which is distal relative to the knee, and wherein proximal means closer to (and distal means farther from) the person's heart when the person is in Vitruvian Man configuration; (b) a first inertial motion sensor which is incorporated into (or attached to) the leg at the first cross-sectional circumference; (c) a second inertial motion sensor which is incorporated into (or attached to) the leg at the second cross-sectional circumference; (d) a first strain (and/or bend) sensor which is incorporated into (or attached to) the leg and spans the knee between the first cross-sectional circumference and the second cross-sectional circumference, and wherein the first strain sensor collects data concerning the transmission of electromagnetic energy through the first strain sensor; (e) a second strain (and/or bend) sensor which is incorporated into (or attached to) the leg and spans the knee between the first cross-sectional circumference and the second cross-sectional circumference, and wherein the second strain sensor collects data concerning the transmission of electromagnetic energy through the second strain sensor; (f) an EMG (electromyographic) sensor which is incorporated into (or attached to) the leg and is in electromagnetic communication with a muscle which moves the knee and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the knee.

In an example, a device or system for capturing human motion can comprise: (a) a shirt worn by a person, wherein a sleeve of the shirt has a longitudinal axis which spans an elbow, wherein the sleeve has a first cross-sectional circumference which is proximal relative to the elbow, wherein the sleeve has a second cross-sectional circumference which is distal relative to the elbow, and wherein proximal means closer to (and distal means farther from) the person's heart when the person is in Vitruvian Man configuration; (b) a first inertial motion sensor which is incorporated into (or attached to) the sleeve at the first cross-sectional circumference; (c) a second inertial motion sensor which is incorporated into (or attached to) the sleeve at the second cross-sectional circumference; (d) a first strain (and/or bend) sensor which is incorporated into (or attached to) the sleeve and spans the elbow between the first cross-sectional circumference and the second cross-sectional circumference, and wherein the first strain sensor collects data concerning the transmission of energy through the first strain sensor; (e) a second strain (and/or bend) sensor which is incorporated into (or attached to) the sleeve and spans the elbow between the first cross-sectional circumference and the second cross-sectional circumference, and wherein the second strain sensor collects data concerning the transmission of energy through the second strain sensor; (f) an EMG (electromyographic) sensor which is incorporated into (or attached to) an elastic band on the proximal (e.g. upper arm) portion of the sleeve and is in electromagnetic communication with a muscle which moves the elbow and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the elbow.

In an example, a device or system for capturing human motion can comprise: (a) a shirt worn by a person, wherein a portion of the shirt has a longitudinal axis which spans a shoulder, wherein the portion has a first cross-sectional circumference which is proximal relative to the shoulder, wherein the portion has a second cross-sectional circumference which is distal relative to the shoulder, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is incorporated into (or attached to) the portion and spans the shoulder between the first cross-sectional circumference and the second cross-sectional circumference, and wherein the first strain sensor collects data concerning the transmission of electromagnetic energy through the first strain sensor; (e) a second strain (and/or bend) sensor which is incorporated into (or attached to) the portion and spans the shoulder between the first cross-sectional circumference and the second cross-sectional circumference, and wherein the second strain sensor collects data concerning the transmission of electromagnetic energy through the second strain sensor; (f) an EMG (electromyographic) sensor which is incorporated into (or attached to) the portion and is in electromagnetic communication with a muscle which moves the shoulder and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the shoulder.

In an example, a device or system for capturing human motion can comprise: (a) a shirt worn by a person, wherein an arm of the shirt has a longitudinal axis which spans an elbow, wherein the arm has a first cross-sectional circumference which is proximal relative to the elbow, wherein the arm has a second cross-sectional circumference which is distal relative to the elbow, and wherein proximal means closer to (and distal means farther from) the person's heart when the person is in Vitruvian Man configuration; (b) a first inertial motion sensor which is incorporated into (or attached to) the arm at the first cross-sectional circumference; (c) a second inertial motion sensor which is incorporated into (or attached to) the arm at the second cross-sectional circumference; (d) a first strain (and/or bend) sensor which is incorporated into (or attached to) the arm and spans the elbow between the first cross-sectional circumference and the second cross-sectional circumference, and wherein the first strain sensor collects data concerning the transmission of electromagnetic energy through the first strain sensor; (e) a second strain (and/or bend) sensor which is incorporated into (or attached to) the arm and spans the elbow between the first cross-sectional circumference and the second cross-sectional circumference, and wherein the second strain sensor collects data concerning the transmission of electromagnetic energy through the second strain sensor; (f) an EMG (electromyographic) sensor which is incorporated into (or attached to) the arm and is in electromagnetic communication with a muscle which moves the elbow and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the elbow.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is incorporated into (or attached to) the portion and spans the body joint between the first cross-sectional circumference and the second cross-sectional circumference, and wherein the first strain sensor collects data concerning the transmission of energy through the first strain sensor; (e) a second strain (and/or bend) sensor which is incorporated into (or attached to) the portion and spans the body joint between the first cross-sectional circumference and the second cross-sectional circumference, and wherein the second strain sensor collects data concerning the transmission of energy through the second strain sensor; (f) an EMG (electromyographic) sensor made with electrically-conductive silver yarn which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is incorporated into (or attached to) the portion and spans the body joint between the first cross-sectional circumference and the second cross-sectional circumference along an orientation which is substantially parallel to the longitudinal axis of the portion, and wherein the first strain sensor collects data concerning the transmission of energy through the first strain sensor; (e) a second strain (and/or bend) sensor which is incorporated into (or attached to) the portion and spans the body joint between the first cross-sectional circumference and the second cross-sectional circumference along an orientation which is substantially orthogonal to the longitudinal axis of the portion, and wherein the second strain sensor collects data concerning the transmission of energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an shirt worn by a person, wherein a torso of the shirt has a longitudinal axis which spans a spinal vertebra, wherein the torso has a first cross-sectional circumference which is proximal relative to the vertebra, wherein the torso has a second cross-sectional circumference which is distal relative to the vertebra, and wherein proximal means closer to (and distal means farther from) the person's heart when the person is in Vitruvian Man configuration; (b) a first inertial motion sensor which is incorporated into (or attached to) the torso at the first cross-sectional circumference; (c) a second inertial motion sensor which is incorporated into (or attached to) the torso at the second cross-sectional circumference; (d) a first strain (and/or bend) sensor which is incorporated into (or attached to) the torso and spans the vertebra between the first cross-sectional circumference and the second cross-sectional circumference, and wherein the first strain sensor collects data concerning the transmission of electromagnetic energy through the first strain sensor; (e) a second strain (and/or bend) sensor which is incorporated into (or attached to) the torso and spans the vertebra between the first cross-sectional circumference and the second cross-sectional circumference, and wherein the second strain sensor collects data concerning the transmission of electromagnetic energy through the second strain sensor; (f) an EMG (electromyographic) sensor which is incorporated into (or attached to) the torso and is in electromagnetic communication with a muscle which moves the vertebra and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the vertebra.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is incorporated into (or attached to) the portion and spans the body joint between the first cross-sectional circumference and the second cross-sectional circumference, wherein the first strain sensor further comprises an electromagnetic energy emitter which is proximal relative to the body joint and an electromagnetic energy receiver which is distal relative to the body joint, and wherein the first strain sensor collects data concerning the transmission of electromagnetic energy through the first strain sensor; (e) a second strain (and/or bend) sensor which is incorporated into (or attached to) the portion and spans the body joint between the first cross-sectional circumference and the second cross-sectional circumference, wherein the second strain sensor further comprises an electromagnetic energy emitter which is proximal relative to the body joint and an electromagnetic energy receiver which is distal relative to the body joint, and wherein the second strain sensor collects data concerning the transmission of electromagnetic energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is incorporated into (or attached to) the portion and spans the body joint between the first cross-sectional circumference and the second cross-sectional circumference, wherein the first strain sensor further comprises an electromagnetic energy emitter which is distal relative to the body joint and an electromagnetic energy receiver which is proximal relative to the body joint, and wherein the first strain sensor collects data concerning the transmission of electromagnetic energy through the first strain sensor; (e) a second strain (and/or bend) sensor which is incorporated into (or attached to) the portion and spans the body joint between the first cross-sectional circumference and the second cross-sectional circumference, wherein the second strain sensor further comprises an electromagnetic energy emitter which is distal relative to the body joint and an electromagnetic energy receiver which is proximal relative to the body joint, and wherein the second strain sensor collects data concerning the transmission of electromagnetic energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is incorporated into (or attached to) the portion and spans the body joint between the first cross-sectional circumference and the second cross-sectional circumference, wherein the first strain sensor further comprises an electromagnetic energy emitter and an electromagnetic energy receiver which are both proximal relative to the body joint, and wherein the first strain sensor collects data concerning the transmission of electromagnetic energy through the first strain sensor; (e) a second strain (and/or bend) sensor which is incorporated into (or attached to) the portion and spans the body joint between the first cross-sectional circumference and the second cross-sectional circumference, wherein the second strain sensor further comprises an electromagnetic energy emitter and an electromagnetic energy receiver which are both proximal relative to the body joint, and wherein the second strain sensor collects data concerning the transmission of electromagnetic energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is incorporated into (or attached to) the portion and spans the body joint between the first cross-sectional circumference and the second cross-sectional circumference, wherein the first strain sensor further comprises an electromagnetic energy emitter and an electromagnetic energy receiver which are both distal relative to the body joint, and wherein the first strain sensor collects data concerning the transmission of electromagnetic energy through the first strain sensor; (e) a second strain (and/or bend) sensor which is incorporated into (or attached to) the portion and spans the body joint between the first cross-sectional circumference and the second cross-sectional circumference, wherein the second strain sensor further comprises an electromagnetic energy emitter and an electromagnetic energy receiver which are both distal relative to the body joint, and wherein the second strain sensor collects data concerning the transmission of electromagnetic energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is incorporated into (or attached to) the portion and spans the body joint between the first cross-sectional circumference and the second cross-sectional circumference in a generally straight line when the portion is extended in Vitruvian Man configuration, and wherein the first strain sensor collects data concerning the transmission of electromagnetic energy through the first strain sensor; (e) a second strain (and/or bend) sensor which is incorporated into (or attached to) the portion and spans the body joint between the first cross-sectional circumference and the second cross-sectional circumference in a generally straight line when the portion is extended in Vitruvian Man configuration, and wherein the second strain sensor collects data concerning the transmission of electromagnetic energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is incorporated into (or attached to) the portion and spans the body joint between the first cross-sectional circumference and the second cross-sectional circumference in a generally straight line when the portion is extended in Vitruvian Man configuration, and wherein the first strain sensor collects data concerning the transmission of electromagnetic energy through the first strain sensor; (e) a second strain (and/or bend) sensor which is incorporated into (or attached to) the portion and spans the body joint between the first cross-sectional circumference and the second cross-sectional circumference in an arcuate manner when the portion is extended in Vitruvian Man configuration, and wherein the second strain sensor collects data concerning the transmission of electromagnetic energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is incorporated into (or attached to) the portion and spans the body joint between the first cross-sectional circumference and the second cross-sectional circumference in a generally straight line when the portion is extended in Vitruvian Man configuration, and wherein the first strain sensor collects data concerning the transmission of electromagnetic energy through the first strain sensor; (e) a second strain (and/or bend) sensor which is incorporated into (or attached to) the portion and spans the body joint between the first cross-sectional circumference and the second cross-sectional circumference in a helical or partial-helical path, and wherein the second strain sensor collects data concerning the transmission of electromagnetic energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is incorporated into (or attached to) the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor which is incorporated into (or attached to) the portion and spans the body joint between the first cross-sectional circumference and the second cross-sectional circumference, wherein the first strain sensor and the second strain sensor are substantially parallel to each other; and wherein the second strain sensor collects data concerning the transmission of electromagnetic energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is incorporated into (or attached to) the portion and spans the body joint between the first cross-sectional circumference and the second cross-sectional circumference, wherein the first strain sensor and the second strain sensor are not parallel to each other and wherein the second strain sensor collects data concerning the transmission of electromagnetic energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is incorporated into (or attached to) the portion and spans the body joint between the first cross-sectional circumference and the second cross-sectional circumference, spanning the body joint at a first angle, and wherein the first strain sensor collects data concerning the transmission of electromagnetic energy through the first strain sensor; (e) a second strain (and/or bend) sensor which is incorporated into (or attached to) the portion and spans the body joint between the first cross-sectional circumference and the second cross-sectional circumference, spanning the body joint at a second angle, wherein the second angle is at least 10 degrees different than the first angle, and wherein the second strain sensor collects data concerning the transmission of electromagnetic energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is incorporated into (or attached to) the portion and spans the dorsal surface of the body joint between the first cross-sectional circumference and the second cross-sectional circumference, and wherein the first strain sensor collects data concerning the transmission of electromagnetic energy through the first strain sensor; (e) a second strain (and/or bend) sensor which is incorporated into (or attached to) the portion and spans the ventral surface of the body joint between the first cross-sectional circumference and the second cross-sectional circumference, and wherein the second strain sensor collects data concerning the transmission of electromagnetic energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is incorporated into (or attached to) the portion and spans the dorsal surface of the body joint between the first cross-sectional circumference and the second cross-sectional circumference, and wherein the first strain sensor collects data concerning the transmission of electromagnetic energy through the first strain sensor; (e) a second strain (and/or bend) sensor which is incorporated into (or attached to) the portion and spans the lateral surface of the body joint between the first cross-sectional circumference and the second cross-sectional circumference, and wherein the second strain sensor collects data concerning the transmission of electromagnetic energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is incorporated into (or attached to) the portion and spans the ventral surface of the body joint between the first cross-sectional circumference and the second cross-sectional circumference, and wherein the first strain sensor collects data concerning the transmission of electromagnetic energy through the first strain sensor; (e) a second strain (and/or bend) sensor which is incorporated into (or attached to) the portion and spans the lateral surface of the body joint between the first cross-sectional circumference and the second cross-sectional circumference, and wherein the second strain sensor collects data concerning the transmission of electromagnetic energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is incorporated into (or attached to) the portion and spans the body joint in a linear manner between the first cross-sectional circumference and the second cross-sectional circumference, and wherein the first strain sensor collects data concerning the transmission of electromagnetic energy through the first strain sensor; (e) a second strain (and/or bend) sensor which is incorporated into (or attached to) the portion and spans the body joint in a (partial) helical manner between the first cross-sectional circumference and the second cross-sectional circumference, and wherein the second strain sensor collects data concerning the transmission of electromagnetic energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is incorporated into (or attached to) the portion and spans the body joint, extending proximally past the first cross-sectional circumference and extending distally past the second cross-sectional circumference, and wherein the first strain sensor collects data concerning the transmission of electromagnetic energy through the first strain sensor; (e) a second strain (and/or bend) sensor which is incorporated into (or attached to) the portion and spans the body joint, extending proximally past the first cross-sectional circumference and extending distally past the second cross-sectional circumference, and wherein the second strain sensor collects data concerning the transmission of electromagnetic energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is incorporated into (or attached to) the portion and spans the body joint between the first cross-sectional circumference and the second cross-sectional circumference, extending between 50% and 90% of the distance between the first cross-sectional circumference and the second cross-sectional circumference, and wherein the first strain sensor collects data concerning the transmission of electromagnetic energy through the first strain sensor; (e) a second strain (and/or bend) sensor which is incorporated into (or attached to) the portion and spans the body joint between the first cross-sectional circumference and the second cross-sectional circumference, extending between 50% and 90% of the distance between the first cross-sectional circumference and the second cross-sectional circumference, and wherein the second strain sensor collects data concerning the transmission of electromagnetic energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is incorporated into (or attached to) the portion and spans the body joint between the first cross-sectional circumference and the second cross-sectional circumference, extending between 10% and 51% of the distance between the first cross-sectional circumference and the second cross-sectional circumference, and wherein the first strain sensor collects data concerning the transmission of electromagnetic energy through the first strain sensor; (e) a second strain (and/or bend) sensor which is incorporated into (or attached to) the portion and spans the body joint between the first cross-sectional circumference and the second cross-sectional circumference, extending between 10% and 51% of the distance between the first cross-sectional circumference and the second cross-sectional circumference, and wherein the second strain sensor collects data concerning the transmission of electromagnetic energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is incorporated into (or attached to) the portion and spans the body joint between the first cross-sectional circumference and the second cross-sectional circumference, extending the entire distance between the first cross-sectional circumference and the second cross-sectional circumference, and wherein the first strain sensor collects data concerning the transmission of electromagnetic energy through the first strain sensor; (e) a second strain (and/or bend) sensor which is incorporated into (or attached to) the portion and spans the body joint between the first cross-sectional circumference and the second cross-sectional circumference, extending the entire distance between the first cross-sectional circumference and the second cross-sectional circumference, and wherein the second strain sensor collects data concerning the transmission of electromagnetic energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is incorporated into (or attached to) the portion and spans the body joint between the first cross-sectional circumference and the second cross-sectional circumference, spanning between 25% and 75% of the distance between the first cross-sectional circumference and the second cross-sectional circumference, and wherein the first strain sensor collects data concerning the transmission of electromagnetic energy through the first strain sensor; (e) a second strain (and/or bend) sensor which is incorporated into (or attached to) the portion and spans the body joint between the first cross-sectional circumference and the second cross-sectional circumference, spanning between 75% and 100% of the distance between the first cross-sectional circumference and the second cross-sectional circumference, and wherein the second strain sensor collects data concerning the transmission of electromagnetic energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is incorporated into (or attached to) the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor which is incorporated into (or attached to) the portion and spans the body joint, extending proximally past the first cross-sectional circumference and extending distally past the second cross-sectional circumference, and wherein the second strain sensor collects data concerning the transmission of electromagnetic energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is incorporated into (or attached to) the portion and spans the body joint along a dorsal side of the body joint between the first cross-sectional circumference and the second cross-sectional circumference, and wherein the first strain sensor collects data concerning the transmission of electromagnetic energy through the first strain sensor; (e) a second strain (and/or bend) sensor which is incorporated into (or attached to) the portion and spans the body joint along a ventral side of the body joint between the first cross-sectional circumference and the second cross-sectional circumference, and wherein the second strain sensor collects data concerning the transmission of electromagnetic energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is incorporated into (or attached to) the portion and spans the body joint along a dorsal side of the body joint between the first cross-sectional circumference and the second cross-sectional circumference, and wherein the first strain sensor collects data concerning the transmission of electromagnetic energy through the first strain sensor; (e) a second strain (and/or bend) sensor which is incorporated into (or attached to) the portion and spans the body joint in a partial helical manner, from the dorsal side to the ventral side of the person's body, between the first cross-sectional circumference and the second cross-sectional circumference, and wherein the second strain sensor collects data concerning the transmission of electromagnetic energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is incorporated into (or attached to) the portion and spans the body joint along a ventral side of the body joint between the first cross-sectional circumference and the second cross-sectional circumference, and wherein the first strain sensor collects data concerning the transmission of electromagnetic energy through the first strain sensor; (e) a second strain (and/or bend) sensor which is incorporated into (or attached to) the portion and spans the body joint in a partial helical manner, from the ventral side to the dorsal side of the person's body, between the first cross-sectional circumference and the second cross-sectional circumference, and wherein the second strain sensor collects data concerning the transmission of electromagnetic energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is incorporated into (or attached to) the portion and spans the body joint along a ventral side of the body joint between the first cross-sectional circumference and the second cross-sectional circumference, and wherein the first strain sensor collects data concerning the transmission of electromagnetic energy through the first strain sensor; (e) a second strain (and/or bend) sensor which is incorporated into (or attached to) the portion and spans the body joint in a partial helical manner, from the dorsal side to the ventral side of the person's body, between the first cross-sectional circumference and the second cross-sectional circumference, and wherein the second strain sensor collects data concerning the transmission of electromagnetic energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is incorporated into (or attached to) the portion and spans the body joint along a dorsal side of the body joint between the first cross-sectional circumference and the second cross-sectional circumference, and wherein the first strain sensor collects data concerning the transmission of electromagnetic energy through the first strain sensor; (e) a second strain (and/or bend) sensor which is incorporated into (or attached to) the portion and spans the body joint in a partial helical manner, from the ventral side to the dorsal side of the person's body, between the first cross-sectional circumference and the second cross-sectional circumference, and wherein the second strain sensor collects data concerning the transmission of electromagnetic energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is incorporated into (or attached to) the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor which is incorporated into (or attached to) the portion and spans the body joint between the first cross-sectional circumference and the second cross-sectional circumference, wherein the first strain sensor and the second strain sensor overlap each other, and wherein the second strain sensor collects data concerning the transmission of electromagnetic energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is incorporated into (or attached to) the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor which is incorporated into (or attached to) the portion and spans the body joint between the first cross-sectional circumference and the second cross-sectional circumference, wherein the first strain sensor and the second strain sensor intersect each other, and wherein the second strain sensor collects data concerning the transmission of electromagnetic energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is incorporated into (or attached to) a first layer of the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor which is incorporated into (or attached to) a second layer of the portion and spans the body joint between the first cross-sectional circumference and the second cross-sectional circumference, and wherein the second strain sensor collects data concerning the transmission of electromagnetic energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is incorporated into (or attached to) the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor which is incorporated into (or attached to) the portion and spans the body joint between the first cross-sectional circumference and the second cross-sectional circumference, and wherein the second strain sensor collects data concerning the transmission of electromagnetic energy through the second strain sensor; (f) an EMG (electromyographic) sensor comprising an electromagnetic energy conductivity sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is incorporated into (or attached to) the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor which is incorporated into (or attached to) the portion and spans the body joint between the first cross-sectional circumference and the second cross-sectional circumference, and wherein the second strain sensor collects data concerning the transmission of electromagnetic energy through the second strain sensor; (f) an EMG (electromyographic) sensor comprising an electromagnetic energy capacitance sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is incorporated into (or attached to) the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor which is incorporated into (or attached to) the portion and spans the body joint between the first cross-sectional circumference and the second cross-sectional circumference, and wherein the second strain sensor collects data concerning the transmission of electromagnetic energy through the second strain sensor; (f) an EMG (electromyographic) sensor made with an elastomeric polymer which has been embedded, impregnated, doped, or coated with conductive material which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is incorporated into (or attached to) the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor which is incorporated into (or attached to) the portion and spans the body joint between the first cross-sectional circumference and the second cross-sectional circumference, and wherein the second strain sensor collects data concerning the transmission of electromagnetic energy through the second strain sensor; (f) an EMG (electromyographic) sensor made with polydimethylsiloxane (PDMS) which has been embedded, impregnated, doped, or coated with conductive material which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is incorporated into (or attached to) the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor which is incorporated into (or attached to) the portion and spans the body joint between the first cross-sectional circumference and the second cross-sectional circumference, and wherein the second strain sensor collects data concerning the transmission of electromagnetic energy through the second strain sensor; (f) an EMG (electromyographic) sensor made with polydimethylsiloxane (PDMS) which has been embedded, impregnated, doped, or coated with silver particles which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is incorporated into (or attached to) the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor which is incorporated into (or attached to) the portion and spans the body joint between the first cross-sectional circumference and the second cross-sectional circumference, and wherein the second strain sensor collects data concerning the transmission of electromagnetic energy through the second strain sensor; (f) an EMG (electromyographic) sensor made with polydimethylsiloxane (PDMS) which has been embedded, impregnated, doped, or coated with carbon which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is incorporated into (or attached to) the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor which is incorporated into (or attached to) the portion and spans the body joint between the first cross-sectional circumference and the second cross-sectional circumference, and wherein the second strain sensor collects data concerning the transmission of electromagnetic energy through the second strain sensor; (f) an EMG (electromyographic) sensor made with polyurethane which has been embedded, impregnated, doped, or coated with conductive material which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is incorporated into (or attached to) the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor which is incorporated into (or attached to) the portion and spans the body joint between the first cross-sectional circumference and the second cross-sectional circumference, and wherein the second strain sensor collects data concerning the transmission of electromagnetic energy through the second strain sensor; (f) an EMG (electromyographic) sensor made with polyurethane which has been embedded, impregnated, doped, or coated with silver particles which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is incorporated into (or attached to) the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor which is incorporated into (or attached to) the portion and spans the body joint between the first cross-sectional circumference and the second cross-sectional circumference, and wherein the second strain sensor collects data concerning the transmission of electromagnetic energy through the second strain sensor; (f) an EMG (electromyographic) sensor made with polyurethane which has been embedded, impregnated, doped, or coated with carbon which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is incorporated into (or attached to) the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor which is incorporated into (or attached to) the portion and spans the body joint between the first cross-sectional circumference and the second cross-sectional circumference, and wherein the second strain sensor collects data concerning the transmission of electromagnetic energy through the second strain sensor; (f) an EMG (electromyographic) sensor made with a silicone polymer which has been embedded, impregnated, doped, or coated with conductive material which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is incorporated into (or attached to) the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor which is incorporated into (or attached to) the portion and spans the body joint between the first cross-sectional circumference and the second cross-sectional circumference, and wherein the second strain sensor collects data concerning the transmission of electromagnetic energy through the second strain sensor; (f) an EMG (electromyographic) sensor made with a silicone polymer which has been embedded, impregnated, doped, or coated with silver particles which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is incorporated into (or attached to) the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor which is incorporated into (or attached to) the portion and spans the body joint between the first cross-sectional circumference and the second cross-sectional circumference, and wherein the second strain sensor collects data concerning the transmission of electromagnetic energy through the second strain sensor; (f) an EMG (electromyographic) sensor made with a silicone polymer which has been embedded, impregnated, doped, or coated with carbon which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is incorporated into (or attached to) the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor which is incorporated into (or attached to) the portion and spans the body joint between the first cross-sectional circumference and the second cross-sectional circumference, and wherein the second strain sensor collects data concerning the transmission of electromagnetic energy through the second strain sensor; (f) an EMG (electromyographic) sensor comprising two high-conductivity flexible layers separated by a low-conductivity flexible layer which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is incorporated into (or attached to) the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor which is incorporated into (or attached to) the portion and spans the body joint between the first cross-sectional circumference and the second cross-sectional circumference, and wherein the second strain sensor collects data concerning the transmission of electromagnetic energy through the second strain sensor; (f) an EMG (electromyographic) sensor comprising two high-conductivity flexible layers separated by a space or gap which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is incorporated into (or attached to) the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor which is incorporated into (or attached to) the portion and spans the body joint between the first cross-sectional circumference and the second cross-sectional circumference, and wherein the second strain sensor collects data concerning the transmission of electromagnetic energy through the second strain sensor; (f) an EMG (electromyographic) sensor with alternating high-conductivity and low-conductivity flexible layers which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is incorporated into (or attached to) the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor which is incorporated into (or attached to) the portion and spans the body joint between the first cross-sectional circumference and the second cross-sectional circumference, and wherein the second strain sensor collects data concerning the transmission of electromagnetic energy through the second strain sensor; (f) an EMG (electromyographic) sensor which is woven or knitted into the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is incorporated into (or attached to) the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor which is incorporated into (or attached to) the portion and spans the body joint between the first cross-sectional circumference and the second cross-sectional circumference, and wherein the second strain sensor collects data concerning the transmission of electromagnetic energy through the second strain sensor; (f) an EMG (electromyographic) sensor which is embroidered onto the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is incorporated into (or attached to) the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor which is incorporated into (or attached to) the portion and spans the body joint between the first cross-sectional circumference and the second cross-sectional circumference, and wherein the second strain sensor collects data concerning the transmission of electromagnetic energy through the second strain sensor; (f) an EMG (electromyographic) sensor which is stitched into the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is incorporated into (or attached to) the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor which is incorporated into (or attached to) the portion and spans the body joint between the first cross-sectional circumference and the second cross-sectional circumference, and wherein the second strain sensor collects data concerning the transmission of electromagnetic energy through the second strain sensor; (f) an EMG (electromyographic) sensor which is adhered to the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is incorporated into (or attached to) the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor which is incorporated into (or attached to) the portion and spans the body joint between the first cross-sectional circumference and the second cross-sectional circumference, and wherein the second strain sensor collects data concerning the transmission of electromagnetic energy through the second strain sensor; (f) an EMG (electromyographic) sensor which is inserted into (fabric) channels in the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is incorporated into (or attached to) the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor which is incorporated into (or attached to) the portion and spans the body joint between the first cross-sectional circumference and the second cross-sectional circumference, and wherein the second strain sensor collects data concerning the transmission of electromagnetic energy through the second strain sensor; (f) an EMG (electromyographic) sensor which spans an entire cross-sectional circumference of the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is incorporated into (or attached to) the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor which is incorporated into (or attached to) the portion and spans the body joint between the first cross-sectional circumference and the second cross-sectional circumference, and wherein the second strain sensor collects data concerning the transmission of electromagnetic energy through the second strain sensor; (f) an EMG (electromyographic) sensor which spans between 50% and 75% of a cross-sectional circumference of the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is incorporated into (or attached to) the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor which is incorporated into (or attached to) the portion and spans the body joint between the first cross-sectional circumference and the second cross-sectional circumference, and wherein the second strain sensor collects data concerning the transmission of electromagnetic energy through the second strain sensor; (f) an EMG (electromyographic) sensor which spans between 10% and 51% of a cross-sectional circumference of the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is incorporated into (or attached to) the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor which is incorporated into (or attached to) the portion and spans the body joint between the first cross-sectional circumference and the second cross-sectional circumference, and wherein the second strain sensor collects data concerning the transmission of electromagnetic energy through the second strain sensor; (f) an EMG (electromyographic) sensor which is incorporated into (or attached to) the portion between the body joint and the first cross-sectional circumference and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is incorporated into (or attached to) the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor which is incorporated into (or attached to) the portion and spans the body joint between the first cross-sectional circumference and the second cross-sectional circumference, and wherein the second strain sensor collects data concerning the transmission of electromagnetic energy through the second strain sensor; (f) an EMG (electromyographic) sensor which is incorporated into (or attached to) the portion between the body joint and the second cross-sectional circumference and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is incorporated into (or attached to) the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor which is incorporated into (or attached to) the portion and spans the body joint between the first cross-sectional circumference and the second cross-sectional circumference, and wherein the second strain sensor collects data concerning the transmission of electromagnetic energy through the second strain sensor; (f) an EMG (electromyographic) sensor which is incorporated into (or attached to) the portion at a location which is proximal relative to the first cross-sectional circumference and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is incorporated into (or attached to) the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor which is incorporated into (or attached to) the portion and spans the body joint between the first cross-sectional circumference and the second cross-sectional circumference, and wherein the second strain sensor collects data concerning the transmission of electromagnetic energy through the second strain sensor; (f) an EMG (electromyographic) sensor which is incorporated into (or attached to) the portion at a location which is distal relative to the second cross-sectional circumference and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is incorporated into (or attached to) the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor which is incorporated into (or attached to) the portion and spans the body joint between the first cross-sectional circumference and the second cross-sectional circumference, and wherein the second strain sensor collects data concerning the transmission of electromagnetic energy through the second strain sensor; (f) an EMG (electromyographic) sensor which is incorporated into (or attached to) the ventral side of the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is incorporated into (or attached to) the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor which is incorporated into (or attached to) the portion and spans the body joint between the first cross-sectional circumference and the second cross-sectional circumference, and wherein the second strain sensor collects data concerning the transmission of electromagnetic energy through the second strain sensor; (f) an EMG (electromyographic) sensor which is incorporated into (or attached to) the dorsal side of the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is printed onto incorporated into (or attached to) the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor which is incorporated into (or attached to) the portion and spans the body joint between the first cross-sectional circumference and the second cross-sectional circumference, and wherein the second strain sensor collects data concerning the transmission of electromagnetic energy through the second strain sensor; (f) an EMG (electromyographic) sensor which is printed onto the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is printed onto incorporated into (or attached to) the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor which is incorporated into (or attached to) the portion and spans the body joint between the first cross-sectional circumference and the second cross-sectional circumference, and wherein the second strain sensor collects data concerning the transmission of electromagnetic energy through the second strain sensor; (f) an EMG (electromyographic) sensor made with conductive ink printed onto the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is inserted into (fabric) channels in the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor which is inserted into (fabric) channels in the portion and spans the body joint between the first cross-sectional circumference and the second cross-sectional circumference, and wherein the second strain sensor collects data concerning the transmission of electromagnetic energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which integrated into (or attached to) the portion along a first orientation and spans the body joint between the first cross-sectional circumference and the second cross-sectional circumference, and wherein the first strain sensor collects data concerning the transmission of electromagnetic energy through the first strain sensor; (e) a second strain (and/or bend) sensor which is integrated into (or attached to) the portion along a second orientation, wherein the second orientation is rotated between 2 and 50 degrees relative to the first orientation, and spans the body joint between the first cross-sectional circumference and the second cross-sectional circumference, and wherein the second strain sensor collects data concerning the transmission of electromagnetic energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which integrated into (or attached to) the portion along a first orientation and spans the body joint between the first cross-sectional circumference and the second cross-sectional circumference, and wherein the first strain sensor collects data concerning the transmission of electromagnetic energy through the first strain sensor; (e) a second strain (and/or bend) sensor which is integrated into (or attached to) the portion along a second orientation, wherein the second orientation is rotated 45 degrees relative to the first orientation, and spans the body joint between the first cross-sectional circumference and the second cross-sectional circumference, and wherein the second strain sensor collects data concerning the transmission of electromagnetic energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is printed onto the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor which is printed onto the portion and spans the body joint between the first cross-sectional circumference and the second cross-sectional circumference, and wherein the second strain sensor collects data concerning the transmission of electromagnetic energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is sewn into the portion and spans the body joint between the first cross-sectional circumference and the second cross-sectional circumference, and wherein the first strain sensor collects data concerning the transmission of energy through the first strain sensor; (e) a second strain (and/or bend) sensor which is sewn into the portion and spans the body joint between the first cross-sectional circumference and the second cross-sectional circumference, and wherein the second strain sensor collects data concerning the transmission of energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is stitched into the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor which is stitched into the portion and spans the body joint between the first cross-sectional circumference and the second cross-sectional circumference, and wherein the second strain sensor collects data concerning the transmission of electromagnetic energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is woven or knitted into the textile of the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor which is woven or knitted into the textile of the portion and spans the body joint between the first cross-sectional circumference and the second cross-sectional circumference, and wherein the second strain sensor collects data concerning the transmission of electromagnetic energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor which is woven with a first orientation into the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor which is woven with a second orientation into the portion, wherein the second orientation is rotated between 20 and 50 degrees relative to the first orientation, and spans the body joint between the first cross-sectional circumference and the second cross-sectional circumference, and wherein the second strain sensor collects data concerning the transmission of electromagnetic energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor whose width increases along a first direction and which is incorporated into (or attached to) the portion and spans the body joint between the first cross-sectional circumference and the second cross-sectional circumference, and wherein the first strain sensor collects data concerning the transmission of energy through the first strain sensor; (e) a second strain (and/or bend) sensor whose width increases along a second direction, wherein the second direction is different than the first direction, and which is incorporated into (or attached to) the portion and spans the body joint between the first cross-sectional circumference and the second cross-sectional circumference, and wherein the second strain sensor collects data concerning the transmission of energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor whose width increases along a first direction and which is incorporated into (or attached to) the portion and spans the body joint between the first cross-sectional circumference and the second cross-sectional circumference, and wherein the first strain sensor collects data concerning the transmission of energy through the first strain sensor; (e) a second strain (and/or bend) sensor whose width increases along a second direction, wherein the second direction is opposite the first direction, and which is incorporated into (or attached to) the portion and spans the body joint between the first cross-sectional circumference and the second cross-sectional circumference, and wherein the second strain sensor collects data concerning the transmission of energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor with a rounded (e.g. oval) cross-sectional shape which is incorporated into (or attached to) the portion and spans the body joint between the first cross-sectional circumference and the second cross-sectional circumference, and wherein the first strain sensor collects data concerning the transmission of energy through the first strain sensor; (e) a second strain (and/or bend) sensor with a rounded (e.g. oval) cross-sectional shape which is incorporated into (or attached to) the portion and spans the body joint between the first cross-sectional circumference and the second cross-sectional circumference, and wherein the second strain sensor collects data concerning the transmission of energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor with a first capacitance level which is incorporated into (or attached to) the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor with a second capacitance level which is incorporated into (or attached to) the portion and spans the body joint between the first cross-sectional circumference and the second cross-sectional circumference, wherein the second capacitance level is greater than the first capacitance level, and wherein the second strain sensor collects data concerning the transmission of electromagnetic energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor with a first conductivity level which is incorporated into (or attached to) the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor with a second conductivity level which is incorporated into (or attached to) the portion and spans the body joint between the first cross-sectional circumference and the second cross-sectional circumference, wherein the second conductivity level is greater than the first conductivity level, and wherein the second strain sensor collects data concerning the transmission of electromagnetic energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor with a first cross-sectional shape which is incorporated into (or attached to) the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor with a second cross-sectional shape which is incorporated into (or attached to) the portion and spans the body joint between the first cross-sectional circumference and the second cross-sectional circumference, wherein the second cross-sectional shape is different than the first cross-sectional shape, and wherein the second strain sensor collects data concerning the transmission of electromagnetic energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor with a first direction of increasing cross-sectional size which is incorporated into (or attached to) the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor with a second direction of increasing cross-sectional size which is incorporated into (or attached to) the portion and spans the body joint between the first cross-sectional circumference and the second cross-sectional circumference, wherein the second direction is different than the first direction, and wherein the second strain sensor collects data concerning the transmission of electromagnetic energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor with a first elasticity level which is incorporated into (or attached to) the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor with a second elasticity level which is incorporated into (or attached to) the portion and spans the body joint between the first cross-sectional circumference and the second cross-sectional circumference, wherein the second elasticity level is greater than the first elasticity level, and wherein the second strain sensor collects data concerning the transmission of electromagnetic energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor with a first length which is incorporated into (or attached to) the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor with a second length which is incorporated into (or attached to) the portion and spans the body joint between the first cross-sectional circumference and the second cross-sectional circumference, wherein the second length is greater than the first length, and wherein the second strain sensor collects data concerning the transmission of electromagnetic energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor with a first pattern of longitudinal variation in cross-sectional shape which is incorporated into (or attached to) the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor with a second pattern of variation in cross-sectional shape which is incorporated into (or attached to) the portion and spans the body joint between the first cross-sectional circumference and the second cross-sectional circumference, wherein the second pattern is different than the first pattern, and wherein the second strain sensor collects data concerning the transmission of electromagnetic energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor with a first resistance level which is incorporated into (or attached to) the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor with a second resistance level which is incorporated into (or attached to) the portion and spans the body joint between the first cross-sectional circumference and the second cross-sectional circumference, wherein the second resistance level is greater than the first resistance level, and wherein the second strain sensor collects data concerning the transmission of electromagnetic energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor with a first shore value which is incorporated into (or attached to) the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor with a second shore value which is incorporated into (or attached to) the portion and spans the body joint between the first cross-sectional circumference and the second cross-sectional circumference, wherein the second shore value is different than the first shore, and wherein the second strain sensor collects data concerning the transmission of electromagnetic energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first strain (and/or bend) sensor with a first width which is incorporated into (or attached to) the portion and spans the body joint between the first cross-sectional circumference and the second cross-sectional circumference, and wherein the first strain sensor collects data concerning the transmission of electromagnetic energy through the first strain sensor; (e) a second strain (and/or bend) sensor with a second width which is incorporated into (or attached to) the portion and spans the body joint between the first cross-sectional circumference and the second cross-sectional circumference, wherein the second width is greater than the first width, and wherein the second strain sensor collects data concerning the transmission of electromagnetic energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

In an example, a device or system for capturing human motion can comprise: (a) an article of clothing worn by a person, wherein a portion of the article of clothing has a longitudinal axis which spans a body joint, wherein the portion has a first cross-sectional circumference which is proximal relative to the body joint, wherein the portion has a second cross-sectional circumference which is distal relative to the body joint, and wherein proximal means closer to (and distal means farther from) the person's heart when the person is in Vitruvian Man configuration; (b) a first inertial motion sensor which is incorporated into (or attached to) the portion at the first cross-sectional circumference; (c) a second inertial motion sensor which is incorporated into (or attached to) the portion at the second cross-sectional circumference; (d) a first undulating (e.g. sinusoidal or zigzag) strain (and/or bend) sensor which is incorporated into (or attached to) the portion and spans the body joint between the first cross-sectional circumference and the second cross-sectional circumference, and wherein the first strain sensor collects data concerning the transmission of energy through the first strain sensor; (e) a second undulating (e.g. sinusoidal or zigzag) strain (and/or bend) sensor which is incorporated into (or attached to) the portion and spans the body joint between the first cross-sectional circumference and the second cross-sectional circumference, and wherein the second strain sensor collects data concerning the transmission of energy through the second strain sensor; (f) an EMG (electromyographic) sensor which is incorporated into (or attached to) the portion and is in electromagnetic communication with a muscle which moves the body joint and/or with nerves which innervate the muscle, and wherein the EMG sensor collects data concerning electromagnetic energy emitted by the muscle and/or the nerves; and (g) a data processor which analyzes data from the first inertial motion sensor, the second inertial motion sensor, the first strain sensor, the second strain sensor, and the EMG sensor to measure a configuration and/or motion of the body joint.

Electromagnetic energy sensors can be incorporated into smart clothing to measure changes in a person's body configuration and/or changes in their muscle activity. Elastic electromagnetic stretch (or bend) sensors can longitudinally span body joints. Stretching (or bending) of these sensors changes the transmission of electromagnetic energy through them which, in turn, can be used to measure and model changes in joint angle and/or rotation. EMG (electromyographic) sensors can be placed along the surface of a person's body in proximity to selected groups of body muscles. Patterns of electromagnetic energy emitted by the muscles and/or the nerves which enervate the muscles are recorded by the sensors which, in turn, can be used to measure and model muscle activity.

In an example, electromagnetic energy sensors can comprise conductive threads, yarns, or fibers which are sewn, woven, or embroidered into smart clothing. In an example, conductive threads, yarns, or fibers can be made from relatively non-conductive material (such as cotton or wool) which is coated or impregnated with conductive material (such as carbon, silver, or aluminum). In an example, electromagnetic energy sensors can comprise longitudinal strips, fibers, channels, or tubes of conductive elastomeric material. In an example, conductive elastomeric material can be made from relatively non-conductive elastomeric material (such as polydimethylsiloxane or PDMS) which is impregnated, doped, or coated with conductive material (such as carbon, silver, or aluminum). In an example, electromagnetic energy sensors can be created by printing patterns onto clothing fabric using conductive ink or resin.

In an example, an electromagnetic stretch (or bend) sensor can be configured to longitudinally span the ventral surface of a person's knee or hip. In an example, an electromagnetic stretch (or bend) sensor can be configured to spiral around a person's knee or hip. In an example, an electromagnetic stretch (or bend) sensor can be configured in a half-spiral around a person's knee or hip. In an example, an electromagnetic stretch (or bend) sensor can be configured to longitudinally span the dorsal surface of a person's elbow or shoulder. In an example, an electromagnetic stretch (or bend) sensor can be configured to spiral around a person's elbow or shoulder. In an example, an electromagnetic stretch (or bend) sensor can be configured in a half-spiral around a person's elbow or shoulder.

In an example, smart clothing can comprise: an article of clothing which is configured to be worn over a person's arm and/or leg; and an electromagnetic stretch (or bend) sensor comprising a non-conductive polymer (such as PDMS) which has been impregnated, doped, embedded, or coated with metal particles or nanostructures (such as carbon particles or nanostructures); wherein the stretch sensor longitudinally spans an elbow, knee, shoulder, or hip. In an example, smart clothing can comprise: an article of clothing which is configured to be worn over a person's arm and/or leg; and an electromagnetic stretch (or bend) sensor comprising a non-conductive polymer (such as PDMS) which has been impregnated, doped, embedded, or coated with metal particles or nanostructures (such as carbon particles or nanostructures); wherein the stretch sensor spirals around an elbow, knee, shoulder, or hip. In an example, smart clothing can comprise: an article of clothing which is configured to be worn over a person's arm and/or leg; and an EMG (electromyographic) sensor made with a non-conductive polymer (such as PDMS) which has been impregnated, doped, embedded, or coated with metal particles or nanostructures (such as carbon particles or nanostructures); wherein the EMG sensor spans between 5% and 55% of the circumference of the arm or leg.

In an example, smart clothing can comprise: an article of clothing which is configured to be worn over a person's arm and/or leg; and an electromagnetic stretch (or bend) sensor comprising conductive threads or yarns; wherein the stretch sensor longitudinally spans an elbow, knee, shoulder, or hip. In an example, smart clothing can comprise: an article of clothing which is configured to be worn over a person's arm and/or leg; and an electromagnetic stretch (or bend) sensor comprising conductive threads or yarns; wherein the stretch sensor spirals around an elbow, knee, shoulder, or hip. In an example, smart clothing can comprise: an article of clothing which is configured to be worn over a person's arm and/or leg; and an EMG (electromyographic) sensor comprising conductive threads or yarns; wherein the EMG sensor spans between 5% and 55% of the circumference of the arm or leg.

In an example, smart clothing can comprise: an article of clothing which is configured to be worn over a person's arm and/or leg; and an electromagnetic stretch (or bend) sensor comprising elastic conductive ink or resin which is printed onto the article of clothing; wherein the stretch sensor longitudinally spans an elbow, knee, shoulder, or hip. In an example, smart clothing can comprise: an article of clothing which is configured to be worn over a person's arm and/or leg; and an electromagnetic stretch (or bend) sensor comprising elastic conductive ink or resin which is printed onto the article of clothing; wherein the stretch sensor spirals around an elbow, knee, shoulder, or hip. In an example, smart clothing can comprise: an article of clothing which is configured to be worn over a person's arm and/or leg; and an EMG (electromyographic) sensor comprising elastic conductive ink or resin which is printed onto the article of clothing; wherein the EMG sensor spans between 5% and 55% of the circumference of the arm or leg.

In an example, smart clothing can comprise: a short-sleeve shirt with distal cuffs or elastic bands; and EMG (electromyographic) sensors which are sewn or woven into the distal cuffs or elastic bands, wherein the EMG sensors span between 5% and 55% of the circumference of the distal cuffs or elastic bands. In an example, smart clothing can comprise: a short-sleeve shirt with distal cuffs or elastic bands; and EMG (electromyographic) sensors which are sewn or woven into the distal cuffs or elastic bands, wherein the EMG sensors span the entire circumference of the distal cuffs or elastic bands. In an example, smart clothing can comprise: pair of shorts (short pants) with distal cuffs or elastic bands; and EMG (electromyographic) sensors which are sewn or woven into the distal cuffs or elastic bands, wherein the EMG sensors span between 5% and 55% of the circumference of the distal cuffs or elastic bands. In an example, smart clothing can comprise: pair of shorts (short pants) with distal cuffs or elastic bands; and EMG (electromyographic) sensors which are sewn or woven into the distal cuffs or elastic bands, wherein the EMG sensors span the entire circumference of the distal cuffs or elastic bands.

In an example, smart clothing can comprise: an article of clothing which is configured to be worn over a person's arm and/or leg; and an electromagnetic stretch (or bend) sensor comprising latex impregnated (or doped, embedded, or coated) with niobium; wherein the stretch sensor spirals around an elbow and/or a knee. Alternatively, smart clothing can comprise: an article of clothing worn over a person's arm and/or leg; and an electromagnetic stretch (or bend) sensor comprising silk thread coated (or embedded) with silver (or sliver alloy, silver chloride) particles or pieces; wherein the stretch sensor spirals around an elbow and/or a knee. In an example, it can form a half-spiral around an elbow and/or a knee. Smart clothing can comprise: an article of clothing worn over a person's arm and/or leg; and an electromagnetic stretch (or bend) sensor comprising cellulose, hydroxypropyl cellulose, and/or hydroxypropyl methylcellulose (HPMC) impregnated (or doped, embedded, or coated) with steel particles or pieces; wherein the stretch sensor longitudinally spans the dorsal surface of an elbow and/or the ventral surface of a knee.

In an example, smart clothing can comprise: an article of clothing which is configured to be worn over a person's arm and/or leg; and an EMG (electromyographic) sensor comprising acetate (thread or yarn) coated (or embedded) with aluminum (or aluminum alloy); wherein the EMG sensor spans between 5% and 55% of the circumference of the arm or leg. In an example, it can span between 25% and 50% of the circumference of the arm or leg. Alternatively, smart clothing can comprise: an article of clothing worn over a person's arm and/or leg; and an EMG (electromyographic) sensor comprising polypropylene glycol impregnated (or doped, embedded, or coated) with carbon (particles, nanotubes, microstructures, graphene, graphite); wherein the EMG sensor spans between 5% and 55% of the circumference of the arm or leg.

In an example, smart clothing can comprise: an article of clothing worn over a person's arm and/or leg; and an EMG sensor printed onto the article of clothing with a polydimethylsiloxane PDMS-based ink which has been impregnated (or doped) with conductive metal particles, pieces, or microstructures; wherein the EMG sensor spans between 10% and 60% of the circumference of the arm or leg. Smart clothing can comprise: an article of clothing; and an EMG sensor comprising stretchable thread or yarn coated (or embedded) with copper (or copper alloy); wherein the EMG sensor is woven, sewn, or embroidered into the article of clothing. Smart clothing can comprise: an article of clothing; and an EMG sensor comprising rubber impregnated (or doped, embedded, or coated) with gallium; wherein the EMG sensor is sewn onto, woven into, adhered to, inserted into, or otherwise attached to the article of clothing. Smart clothing can comprise: an article of clothing; and an EMG sensor comprising nylon (thread or yarn) coated (or embedded) with gold (or gold alloy) particles or pieces. Alternatively, smart clothing can comprise: an article of clothing; and an EMG sensor comprising stretchable thread or yarn coated (or embedded) with nickel (or nickel alloy) particles or pieces. Smart clothing can comprise: an article of clothing worn over a person's arm and/or leg; and an electromagnetic stretch (or bend) sensor comprising acrylic (yarn, thread, or fiber) coated (or embedded) with niobium; wherein the stretch sensor spirals around an elbow and/or a knee.

In an example, smart clothing can comprise: an article of clothing worn over a person's arm and/or leg; and an electromagnetic stretch (or bend) sensor comprising cotton (thread or fiber) coated (or embedded) with silver (or sliver alloy, silver chloride); wherein the stretch sensor spirals around an elbow and/or a knee. Alternatively, smart clothing can comprise: an article of clothing worn over a person's arm and/or leg; and an electromagnetic stretch (or bend) sensor comprising hydrogel impregnated (or doped, embedded, or coated) with niobium; wherein the stretch sensor spirals around an elbow and/or a knee. Smart clothing can comprise: an article of clothing worn over a person's arm and/or leg; and an electromagnetic stretch (or bend) sensor comprising nylon (thread or yarn) coated (or embedded) with tungsten particles or pieces; wherein the stretch sensor spirals around an elbow and/or a knee.

Smart clothing can comprise: an article of clothing which is configured to be worn over a person's arm and/or leg; and an electromagnetic stretch (or bend) sensor comprising polyester (thread or yarn) coated (or embedded) with niobium; wherein the stretch sensor spirals around an elbow and/or a knee. In an example, it can form a half-spiral around an elbow and/or a knee. Alternatively, smart clothing can comprise: an article of clothing worn over a person's arm and/or leg; and an electromagnetic stretch (or bend) sensor comprising polystyrene (PST) impregnated (or doped, embedded, or coated) with silver (or sliver alloy, silver chloride); wherein the stretch sensor spirals around an elbow and/or a knee. Smart clothing can comprise: an article of clothing worn over a person's arm and/or leg; and an electromagnetic stretch (or bend) sensor comprising rayon (thread or yarn) coated (or embedded) with copper (or copper alloy) particles or pieces; wherein the stretch sensor spirals around an elbow and/or a knee.

In an example, smart clothing can comprise: an article of clothing worn over a person's arm and/or leg; and an electromagnetic stretch (or bend) sensor comprising silicone, silicone rubber, and/or PDMS impregnated (or doped, embedded, or coated) with silver (or sliver alloy, silver chloride) particles or pieces; wherein the stretch sensor spirals around an elbow and/or a knee. Alternatively, smart clothing can comprise: an article of clothing worn over a person's arm and/or leg; and an electromagnetic stretch (or bend) sensor comprising styrene ethylene butylene streyene (SEBS) impregnated (or doped, embedded, or coated) with aluminum (or aluminum alloy); wherein the stretch sensor spirals around an elbow and/or a knee. Smart clothing can comprise: an article of clothing worn over a person's arm and/or leg; and an electromagnetic stretch (or bend) sensor comprising thermoplastic elastomer (TPE), thermoplastic polyurethane (TPU), and/or thermoplastic vulcanizate (TPV) impregnated (or doped, embedded, or coated) with silver (or sliver alloy, silver chloride); wherein the stretch sensor spirals around an elbow and/or a knee. In an example, it can form a half-spiral around an elbow and/or a knee. Smart clothing can comprise: an article of clothing which is configured to be worn over a person's arm and/or leg; and an electromagnetic stretch (or bend) sensor printed onto the article of clothing with a polymer-based ink which has been impregnated (or doped) with steel particles or pieces; wherein the stretch sensor spirals around an elbow and/or a knee. Alternatively, smart clothing can comprise: an article of clothing worn over a person's arm and/or leg; and an electromagnetic stretch (or bend) sensor comprising acetate (thread or yarn) coated (or embedded) with gallium; wherein the stretch sensor longitudinally spans the dorsal surface of an elbow and/or the ventral surface of a knee. Alternatively, smart clothing can comprise: an article of clothing worn over a person's arm and/or leg; and an electromagnetic stretch (or bend) sensor comprising an elastic material and/or an elastomeric polymer impregnated (or doped, embedded, or coated) with steel particles or pieces; wherein the stretch sensor longitudinally spans the dorsal surface of an elbow and/or the ventral surface of a knee.

In an example, smart clothing can comprise: an article of clothing worn over a person's arm and/or leg; and an electromagnetic stretch (or bend) sensor comprising elastane and/or Lycra™ (thread or fiber) coated (or embedded) with steel particles or pieces; wherein the stretch sensor longitudinally spans the dorsal surface of an elbow and/or the ventral surface of a knee. Smart clothing can comprise: an article of clothing worn over a person's arm and/or leg; and an electromagnetic stretch (or bend) sensor comprising hydrogel impregnated (or doped, embedded, or coated) with steel particles or pieces; wherein the stretch sensor longitudinally spans the dorsal surface of an elbow and/or the ventral surface of a knee. Smart clothing can comprise: an article of clothing worn over a person's arm and/or leg; and an electromagnetic stretch (or bend) sensor comprising poly(3,4-ethylenedioxythiophene) polystyrene sulfonate (PEDOT/PSS) impregnated (or doped, embedded, or coated) with tungsten particles or pieces; wherein the stretch sensor longitudinally spans the dorsal surface of an elbow and/or the ventral surface of a knee. Smart clothing can comprise: an article of clothing which is configured to be worn over a person's arm and/or leg; and an electromagnetic stretch (or bend) sensor comprising polypropylene glycol impregnated (or doped, embedded, or coated) with gold (or gold alloy) particles or pieces; wherein the stretch sensor longitudinally spans the dorsal surface of an elbow and/or the ventral surface of a knee. Smart clothing can comprise: an article of clothing worn over a person's arm and/or leg; and an electromagnetic stretch (or bend) sensor comprising polyurethane impregnated (or doped, embedded, or coated) with tungsten particles or pieces; wherein the stretch sensor longitudinally spans the dorsal surface of an elbow and/or the ventral surface of a knee. Alternatively, smart clothing can comprise: an article of clothing worn over a person's arm and/or leg; and an electromagnetic stretch (or bend) sensor comprising polyvinyl alcohol (PVOH) impregnated (or doped, embedded, or coated) with tungsten particles or pieces; wherein the stretch sensor longitudinally spans the dorsal surface of an elbow and/or the ventral surface of a knee.

In another example, smart clothing can comprise: an article of clothing worn over a person's arm and/or leg; and an electromagnetic stretch (or bend) sensor comprising rubber impregnated (or doped, embedded, or coated) with conductive metal particles, pieces, or microstructures; wherein the stretch sensor longitudinally spans the dorsal surface of an elbow and/or the ventral surface of a knee. Alternatively, smart clothing can comprise: an article of clothing worn over a person's arm and/or leg; and an electromagnetic stretch (or bend) sensor comprising silicone, silicone rubber, and/or PDMS impregnated (or doped, embedded, or coated) with tungsten particles or pieces; wherein the stretch sensor longitudinally spans the dorsal surface of an elbow and/or the ventral surface of a knee. Smart clothing can comprise: an article of clothing worn over a person's arm and/or leg; and an electromagnetic stretch (or bend) sensor comprising TPE, TPU, and/or TPV impregnated (or doped, embedded, or coated) with conductive metal particles, pieces, or microstructures; wherein the stretch sensor longitudinally spans the dorsal surface of an elbow and/or the ventral surface of a knee.

Alternatively, smart clothing can comprise: an article of clothing which is configured to be worn over a person's arm and/or leg; and an electromagnetic stretch (or bend) sensor printed onto the article of clothing with a PDMS-based ink which has been impregnated (or doped) with nickel (or nickel alloy) particles or pieces; wherein the stretch sensor longitudinally spans the dorsal surface of an elbow and/or the ventral surface of a knee. Smart clothing can comprise: an article of clothing worn over a person's arm and/or leg; and an electromagnetic stretch (or bend) sensor printed onto the article of clothing with conductive ink or resin which has been impregnated (or doped) with aluminum (or aluminum alloy) particles or pieces; wherein the stretch sensor longitudinally spans the dorsal surface of an elbow and/or the ventral surface of a knee. Smart clothing can comprise: an article of clothing worn over a person's arm and/or leg; and an EMG sensor comprising acrylic (yarn, thread, or fiber) coated (or embedded) with copper (or copper alloy) particles or pieces; wherein the EMG sensor spans between 10% and 60% of the circumference of the arm or leg.

In an example, smart clothing can comprise: an article of clothing worn over a person's arm and/or leg; and an EMG sensor comprising cellulose, hydroxypropyl cellulose, and/or HPMC impregnated (or doped, embedded, or coated) with conductive metal particles, pieces, or microstructures; wherein the EMG sensor spans between 10% and 60% of the circumference of the arm or leg. Smart clothing can comprise: an article of clothing worn over a person's arm and/or leg; and an EMG sensor comprising hydrogel impregnated (or doped, embedded, or coated) with carbon (particles, nanotubes, microstructures, graphene, graphite); wherein the EMG sensor spans between 10% and 60% of the circumference of the arm or leg. Alternatively, smart clothing can comprise: an article of clothing worn over a person's arm and/or leg; and an EMG sensor comprising nylon (thread or yarn) coated (or embedded) with niobium; wherein the EMG sensor spans between 10% and 60% of the circumference of the arm or leg. Smart clothing can comprise: an article of clothing which is configured to be worn over a person's arm and/or leg; and an EMG sensor comprising polyethylene glycol (PEG), polyethylene terephthalate (PET), or polytetrafluoroethylene (PTFE) impregnated (or doped, embedded, or coated) with aluminum (or aluminum alloy) particles or pieces; wherein the EMG sensor spans between 10% and 60% of the circumference of the arm or leg. Alternatively, smart clothing can comprise: an article of clothing worn over a person's arm and/or leg; and an EMG sensor comprising polystyrene (PST) impregnated (or doped, embedded, or coated) with gallium; wherein the EMG sensor spans between 10% and 60% of the circumference of the arm or leg. Smart clothing can comprise: an article of clothing worn over a person's arm and/or leg; and an EMG sensor comprising PVOH impregnated (or doped, embedded, or coated) with carbon (particles, nanotubes, microstructures, graphene, graphite); wherein the EMG sensor spans between 5% and 55% of the circumference of the arm or leg.

In another example, smart clothing can comprise: an article of clothing worn over a person's arm and/or leg; and an EMG sensor comprising silicone, silicone rubber, and/or PDMS impregnated (or doped, embedded, or coated) with carbon (particles, nanotubes, microstructures, graphene, graphite); wherein the EMG sensor spans between 10% and 60% of the circumference of the arm or leg. Smart clothing can comprise: an article of clothing worn over a person's arm and/or leg; and an EMG sensor comprising stretchable thread or yarn coated (or embedded) with silver (or sliver alloy, silver chloride); wherein the EMG sensor spans between 10% and 60% of the circumference of the arm or leg. Smart clothing can comprise: an article of clothing worn over a person's arm and/or leg; and an EMG sensor comprising wool yarn coated (or embedded) with conductive metal particles, pieces, or microstructures; wherein the EMG sensor spans between 10% and 60% of the circumference of the arm or leg.

Alternatively, smart clothing can comprise: an article of clothing which is configured to be worn over a person's arm and/or leg; and an EMG sensor printed onto the article of clothing with a polymer-based ink which has been impregnated (or doped) with gold (or gold alloy); wherein the EMG sensor spans between 10% and 60% of the circumference of the arm or leg. Smart clothing can comprise: an article of clothing worn over a person's arm and/or leg; and an EMG sensor printed onto the article of clothing with conductive ink or resin which has been impregnated (or doped) with conductive metal particles, pieces, or microstructures; wherein the EMG sensor spans between 10% and 60% of the circumference of the arm or leg. Alternatively, smart clothing can comprise: an article of clothing; and an EMG sensor comprising cotton (thread or fiber) coated (or embedded) with niobium; wherein the EMG sensor is woven, sewn, or embroidered into the article of clothing.

In an example, smart clothing can comprise: an article of clothing; and an EMG sensor comprising nylon (thread or yarn) coated (or embedded) with steel particles or pieces; wherein the EMG sensor is woven, sewn, or embroidered into the article of clothing. Smart clothing can comprise: an article of clothing; and an EMG sensor comprising silk thread coated (or embedded) with copper (or copper alloy) particles or pieces; wherein the EMG sensor is woven, sewn, or embroidered into the article of clothing. Alternatively, smart clothing can comprise: an article of clothing; and an EMG sensor comprising wool yarn coated (or embedded) with nickel (or nickel alloy) particles or pieces; wherein the EMG sensor is woven, sewn, or embroidered into the article of clothing. Smart clothing can comprise: an article of clothing; and an EMG sensor comprising cellulose, hydroxypropyl cellulose, and/or HPMC impregnated (or doped, embedded, or coated) with copper (or copper alloy) particles or pieces; wherein the EMG sensor is sewn onto, woven into, adhered to, inserted into, or otherwise attached to the article of clothing. Smart clothing can comprise: an article of clothing; and an EMG sensor comprising poly(3, 4-ethylenedioxythiophene) polystyrene sulfonate (PEDOT/PSS) impregnated (or doped, embedded, or coated) with gallium; wherein the EMG sensor is sewn onto, woven into, adhered to, inserted into, or otherwise attached to the article of clothing. Alternatively, smart clothing can comprise: an article of clothing; and an EMG sensor comprising polypropylene glycol impregnated (or doped, embedded, or coated) with tungsten particles or pieces; wherein the EMG sensor is sewn onto, woven into, adhered to, inserted into, or otherwise attached to the article of clothing.

In another example, smart clothing can comprise: an article of clothing; and an EMG sensor comprising PVOH impregnated (or doped, embedded, or coated) with gallium; wherein the EMG sensor is sewn onto, woven into, adhered to, inserted into, or otherwise attached to the article of clothing. Alternatively, smart clothing can comprise: an article of clothing; and an EMG sensor comprising silicone, silicone rubber, and/or PDMS impregnated (or doped, embedded, or coated) with niobium; wherein the EMG sensor is sewn onto, woven into, adhered to, inserted into, or otherwise attached to the article of clothing. Alternatively, smart clothing can comprise: an article of clothing; and an EMG sensor comprising TPE, TPU, and/or thermoplastic vulcanizate (TPV) impregnated (or doped, embedded, or coated) with gallium; wherein the EMG sensor is sewn onto, woven into, adhered to, inserted into, or otherwise attached to the article of clothing. Smart clothing can comprise: an article of clothing; and an EMG sensor comprising an elastic material and/or an elastomeric polymer impregnated (or doped, embedded, or coated) with gold (or gold alloy) particles or pieces. Smart clothing can comprise: an article of clothing; and an EMG sensor comprising elastane and/or Lycra™ (thread or fiber) coated (or embedded) with tungsten particles or pieces. Smart clothing can comprise: an article of clothing; and an EMG sensor comprising latex impregnated (or doped, embedded, or coated) with gold (or gold alloy) particles or pieces.

In an example, smart clothing can comprise: an article of clothing; and an EMG sensor comprising PEDOT/PSS impregnated (or doped, embedded, or coated) with silver (or sliver alloy, silver chloride) particles or pieces. Alternatively, smart clothing can comprise: an article of clothing; and an EMG sensor comprising polyethylene glycol (PEG), polyethylene terephthalate (PET), or polytetrafluoroethylene (PTFE) impregnated (or doped, embedded, or coated) with gold (or gold alloy) particles or pieces. Alternatively, smart clothing can comprise: an article of clothing; and an EMG sensor comprising polyurethane impregnated (or doped, embedded, or coated) with nickel (or nickel alloy) particles or pieces. Smart clothing can comprise: an article of clothing; and an EMG sensor comprising rubber impregnated (or doped, embedded, or coated) with carbon (particles, nanotubes, microstructures, graphene, graphite). Alternatively, smart clothing can comprise: an article of clothing; and an EMG sensor comprising silk thread coated (or embedded) with nickel (or nickel alloy) particles or pieces. Smart clothing can comprise: an article of clothing; and an EMG sensor comprising SEBS impregnated (or doped, embedded, or coated) with steel particles or pieces.

In another example, smart clothing can comprise: an article of clothing; and an EMG sensor comprising wool yarn coated (or embedded) with nickel (or nickel alloy) particles or pieces. Alternatively, smart clothing can comprise: an article of clothing; and an EMG sensor printed onto the article of clothing with a silicone-based ink which has been impregnated (or doped) with niobium. Smart clothing can comprise: an article of clothing worn over a person's arm and/or leg; and an electromagnetic stretch (or bend) sensor comprising an elastic material and/or an elastomeric polymer impregnated (or doped, embedded, or coated) with carbon (particles, nanotubes, microstructures, graphene, graphite); wherein the stretch sensor spirals around an elbow and/or a knee. Smart clothing can comprise: an article of clothing worn over a person's arm and/or leg; and an electromagnetic stretch (or bend) sensor comprising elastane and/or Lycra™ (thread or fiber) coated (or embedded) with steel particles or pieces; wherein the stretch sensor spirals around an elbow and/or a knee. Smart clothing can comprise: an article of clothing worn over a person's arm and/or leg; and an electromagnetic stretch (or bend) sensor comprising nylon (thread or yarn) coated (or embedded) with carbon (particles, nanotubes, microstructures, graphene, graphite); wherein the stretch sensor spirals around an elbow and/or a knee. In an example, it can form a half-spiral around an elbow and/or a knee. Alternatively, smart clothing can comprise: an article of clothing worn over a person's arm and/or leg; and an electromagnetic stretch (or bend) sensor comprising polyurethane impregnated (or doped, embedded, or coated) with conductive metal particles, pieces, or microstructures; wherein the stretch sensor spirals around an elbow and/or a knee.

In an example, smart clothing can comprise: an article of clothing which is configured to be worn over a person's arm and/or leg; and an electromagnetic stretch (or bend) sensor comprising rubber impregnated (or doped, embedded, or coated) with conductive metal particles, pieces, or microstructures; wherein the stretch sensor spirals around an elbow and/or a knee. Smart clothing can comprise: an article of clothing worn over a person's arm and/or leg; and an electromagnetic stretch (or bend) sensor comprising stretchable thread or yarn coated (or embedded) with conductive metal particles, pieces, or microstructures; wherein the stretch sensor spirals around an elbow and/or a knee. Alternatively, smart clothing can comprise: an article of clothing which is configured to be worn over a person's arm and/or leg; and an electromagnetic stretch (or bend) sensor printed onto the article of clothing with a silicone-based ink which has been impregnated (or doped) with copper (or copper alloy) particles or pieces; wherein the stretch sensor spirals around an elbow and/or a knee. Smart clothing can comprise: an article of clothing worn over a person's arm and/or leg; and an electromagnetic stretch (or bend) sensor comprising acrylic (yarn, thread, or fiber) coated (or embedded) with copper (or copper alloy) particles or pieces; wherein the stretch sensor longitudinally spans the dorsal surface of an elbow and/or the ventral surface of a knee.

Smart clothing can comprise: an article of clothing which is configured to be worn over a person's arm and/or leg; and an electromagnetic stretch (or bend) sensor comprising cotton (thread or fiber) coated (or embedded) with niobium; wherein the stretch sensor longitudinally spans the dorsal surface of an elbow and/or the ventral surface of a knee. Alternatively, smart clothing can comprise: an article of clothing worn over a person's arm and/or leg; and an electromagnetic stretch (or bend) sensor comprising polyester (thread or yarn) coated (or embedded) with gallium; wherein the stretch sensor longitudinally spans the dorsal surface of an elbow and/or the ventral surface of a knee.

In another example, smart clothing can comprise: an article of clothing worn over a person's arm and/or leg; and an electromagnetic stretch (or bend) sensor comprising polystyrene (PST) impregnated (or doped, embedded, or coated) with gallium; wherein the stretch sensor longitudinally spans the dorsal surface of an elbow and/or the ventral surface of a knee. Alternatively, smart clothing can comprise: an article of clothing worn over a person's arm and/or leg; and an electromagnetic stretch (or bend) sensor comprising rayon (thread or yarn) coated (or embedded) with gallium; wherein the stretch sensor longitudinally spans the dorsal surface of an elbow and/or the ventral surface of a knee. Smart clothing can comprise: an article of clothing worn over a person's arm and/or leg; and an electromagnetic stretch (or bend) sensor comprising TPE, TPU, and/or TPV impregnated (or doped, embedded, or coated) with gold (or gold alloy) particles or pieces; wherein the stretch sensor longitudinally spans the dorsal surface of an elbow and/or the ventral surface of a knee. Smart clothing can comprise: an article of clothing which is configured to be worn over a person's arm and/or leg; and an electromagnetic stretch (or bend) sensor printed onto the article of clothing with a polymer-based ink which has been impregnated (or doped) with gold (or gold alloy) particles or pieces; wherein the stretch sensor longitudinally spans the dorsal surface of an elbow and/or the ventral surface of a knee. Smart clothing can comprise: an article of clothing worn over a person's arm and/or leg; and an EMG sensor comprising acetate (thread or yarn) coated (or embedded) with gold (or gold alloy); wherein the EMG sensor spans between 10% and 60% of the circumference of the arm or leg. Alternatively, smart clothing can comprise: an article of clothing worn over a person's arm and/or leg; and an EMG sensor comprising hydrogel impregnated (or doped, embedded, or coated) with nickel (or nickel alloy) particles or pieces; wherein the EMG sensor spans between 5% and 55% of the circumference of the arm or leg.

In an example, smart clothing can comprise: an article of clothing worn over a person's arm and/or leg; and an EMG sensor comprising PEDOT/PSS impregnated (or doped, embedded, or coated) with nickel (or nickel alloy) particles or pieces; wherein the EMG sensor spans between 10% and 60% of the circumference of the arm or leg. Alternatively, smart clothing can comprise: an article of clothing which is configured to be worn over a person's arm and/or leg; and an EMG sensor comprising polypropylene glycol impregnated (or doped, embedded, or coated) with nickel (or nickel alloy); wherein the EMG sensor spans between 10% and 60% of the circumference of the arm or leg. Smart clothing can comprise: an article of clothing which is configured to be worn over a person's arm and/or leg; and an EMG sensor comprising silicone, silicone rubber, and/or PDMS impregnated (or doped, embedded, or coated) with niobium; wherein the EMG sensor spans between 10% and 60% of the circumference of the arm or leg. Alternatively, smart clothing can comprise: an article of clothing worn over a person's arm and/or leg; and an EMG sensor comprising SEBS impregnated (or doped, embedded, or coated) with niobium; wherein the EMG sensor spans between 10% and 60% of the circumference of the arm or leg. Smart clothing can comprise: an article of clothing which is configured to be worn over a person's arm and/or leg; and an EMG sensor printed onto the article of clothing with a PDMS-based ink which has been impregnated (or doped) with niobium; wherein the EMG sensor spans between 10% and 60% of the circumference of the arm or leg. Alternatively, smart clothing can comprise: an article of clothing; and an EMG sensor comprising cotton (thread or fiber) coated (or embedded) with conductive metal particles, pieces, or microstructures; wherein the EMG sensor is woven, sewn, or embroidered into the article of clothing.

In an example, smart clothing can comprise: an article of clothing; and an EMG sensor comprising polyester (thread or yarn) coated (or embedded) with silver (or sliver alloy, silver chloride) particles or pieces; wherein the EMG sensor is woven, sewn, or embroidered into the article of clothing. Smart clothing can comprise: an article of clothing; and an EMG sensor comprising stretchable thread or yarn coated (or embedded) with silver (or sliver alloy, silver chloride) particles or pieces; wherein the EMG sensor is woven, sewn, or embroidered into the article of clothing. Alternatively, smart clothing can comprise: an article of clothing; and an EMG sensor comprising PEDOT/PSS impregnated (or doped, embedded, or coated) with steel particles or pieces; wherein the EMG sensor is sewn onto, woven into, adhered to, inserted into, or otherwise attached to the article of clothing. Smart clothing can comprise: an article of clothing; and an EMG sensor comprising polystyrene (PST) impregnated (or doped, embedded, or coated) with steel particles or pieces; wherein the EMG sensor is sewn onto, woven into, adhered to, inserted into, or otherwise attached to the article of clothing. Smart clothing can comprise: an article of clothing; and an EMG sensor comprising rubber impregnated (or doped, embedded, or coated) with steel particles or pieces; wherein the EMG sensor is sewn onto, woven into, adhered to, inserted into, or otherwise attached to the article of clothing. Alternatively, smart clothing can comprise: an article of clothing; and an EMG sensor comprising an elastic material and/or an elastomeric polymer impregnated (or doped, embedded, or coated) with tungsten particles or pieces.

In an example, smart clothing can comprise: an article of clothing; and an EMG sensor comprising elastane and/or Lycra™ (thread or fiber) coated (or embedded) with aluminum (or aluminum alloy) particles or pieces. Smart clothing can comprise: an article of clothing; and an EMG sensor comprising nylon (thread or yarn) coated (or embedded) with tungsten particles or pieces. Alternatively, smart clothing can comprise: an article of clothing; and an EMG sensor comprising PVOH impregnated (or doped, embedded, or coated) with aluminum (or aluminum alloy) particles or pieces. Smart clothing can comprise: an article of clothing; and an EMG sensor comprising silicone, silicone rubber, and/or PDMS impregnated (or doped, embedded, or coated) with conductive metal particles, pieces, or microstructures. Alternatively, smart clothing can comprise: an article of clothing; and an EMG sensor comprising SEBS impregnated (or doped, embedded, or coated) with aluminum (or aluminum alloy) particles or pieces. Smart clothing can comprise: an article of clothing; and an EMG sensor printed onto the article of clothing with conductive ink or resin which has been impregnated (or doped) with carbon (particles, nanotubes, microstructures, graphene, graphite).

In another example, smart clothing can comprise: an article of clothing worn over a person's arm and/or leg; and an electromagnetic stretch (or bend) sensor comprising acrylic (yarn, thread, or fiber) coated (or embedded) with tungsten particles or pieces; wherein the stretch sensor spirals around an elbow and/or a knee. In an example, it can form a half-spiral around an elbow and/or a knee. Smart clothing can comprise: an article of clothing worn over a person's arm and/or leg; and an electromagnetic stretch (or bend) sensor comprising cellulose, hydroxypropyl cellulose, and/or HPMC impregnated (or doped, embedded, or coated) with niobium; wherein the stretch sensor spirals around an elbow and/or a knee. Smart clothing can comprise: an article of clothing worn over a person's arm and/or leg; and an electromagnetic stretch (or bend) sensor comprising nylon (thread or yarn) coated (or embedded) with niobium; wherein the stretch sensor spirals around an elbow and/or a knee. Alternatively, smart clothing can comprise: an article of clothing which is configured to be worn over a person's arm and/or leg; and an electromagnetic stretch (or bend) sensor comprising polyethylene glycol (PEG), polyethylene terephthalate (PET), or polytetrafluoroethylene (PTFE) impregnated (or doped, embedded, or coated) with aluminum (or aluminum alloy) particles or pieces; wherein the stretch sensor spirals around an elbow and/or a knee. Smart clothing can comprise: an article of clothing worn over a person's arm and/or leg; and an electromagnetic stretch (or bend) sensor comprising polyurethane impregnated (or doped, embedded, or coated) with aluminum (or aluminum alloy) particles or pieces; wherein the stretch sensor spirals around an elbow and/or a knee. In an example, it can form a half-spiral around an elbow and/or a knee. Alternatively, smart clothing can comprise: an article of clothing worn over a person's arm and/or leg; and an electromagnetic stretch (or bend) sensor comprising PVOH impregnated (or doped, embedded, or coated) with silver (or sliver alloy, silver chloride) particles or pieces; wherein the stretch sensor spirals around an elbow and/or a knee.

In an example, smart clothing can comprise: an article of clothing worn over a person's arm and/or leg; and an electromagnetic stretch (or bend) sensor comprising stretchable thread or yarn coated (or embedded) with silver (or sliver alloy, silver chloride) particles or pieces; wherein the stretch sensor spirals around an elbow and/or a knee. Smart clothing can comprise: an article of clothing which is configured to be worn over a person's arm and/or leg; and an electromagnetic stretch (or bend) sensor comprising wool yarn coated (or embedded) with conductive metal particles, pieces, or microstructures; wherein the stretch sensor spirals around an elbow and/or a knee. In an example, it can form a half-spiral around an elbow and/or a knee. Smart clothing can comprise: an article of clothing worn over a person's arm and/or leg; and an electromagnetic stretch (or bend) sensor printed onto the article of clothing with a silicone-based ink which has been impregnated (or doped) with carbon (particles, nanotubes, microstructures, graphene, graphite); wherein the stretch sensor spirals around an elbow and/or a knee. Alternatively, smart clothing can comprise: an article of clothing worn over a person's arm and/or leg; and an electromagnetic stretch (or bend) sensor printed onto the article of clothing with conductive ink or resin which has been impregnated (or doped) with steel particles or pieces; wherein the stretch sensor spirals around an elbow and/or a knee. In an example, it can form a half-spiral around an elbow and/or a knee. Smart clothing can comprise: an article of clothing which is configured to be worn over a person's arm and/or leg; and an electromagnetic stretch (or bend) sensor comprising cotton (thread or fiber) coated (or embedded) with carbon (particles, nanotubes, microstructures, graphene, graphite); wherein the stretch sensor longitudinally spans the dorsal surface of an elbow and/or the ventral surface of a knee. Alternatively, smart clothing can comprise: an article of clothing worn over a person's arm and/or leg; and an electromagnetic stretch (or bend) sensor comprising latex impregnated (or doped, embedded, or coated) with copper (or copper alloy) particles or pieces; wherein the stretch sensor longitudinally spans the dorsal surface of an elbow and/or the ventral surface of a knee.

In another example, smart clothing can comprise: an article of clothing worn over a person's arm and/or leg; and an electromagnetic stretch (or bend) sensor comprising polyester (thread or yarn) coated (or embedded) with conductive metal particles, pieces, or microstructures; wherein the stretch sensor longitudinally spans the dorsal surface of an elbow and/or the ventral surface of a knee. Alternatively, smart clothing can comprise: an article of clothing which is configured to be worn over a person's arm and/or leg; and an electromagnetic stretch (or bend) sensor comprising PEG, PET, or PTFE impregnated (or doped, embedded, or coated) with tungsten particles or pieces; wherein the stretch sensor longitudinally spans the dorsal surface of an elbow and/or the ventral surface of a knee. Smart clothing can comprise: an article of clothing worn over a person's arm and/or leg; and an electromagnetic stretch (or bend) sensor comprising rayon (thread or yarn) coated (or embedded) with tungsten particles or pieces; wherein the stretch sensor longitudinally spans the dorsal surface of an elbow and/or the ventral surface of a knee. Smart clothing can comprise: an article of clothing worn over a person's arm and/or leg; and an electromagnetic stretch (or bend) sensor comprising silk thread coated (or embedded) with gallium; wherein the stretch sensor longitudinally spans the dorsal surface of an elbow and/or the ventral surface of a knee. Smart clothing can comprise: an article of clothing which is configured to be worn over a person's arm and/or leg; and an electromagnetic stretch (or bend) sensor comprising TPE, TPU, and/or thermoplastic vulcanizate (TPV) impregnated (or doped, embedded, or coated) with copper (or copper alloy); wherein the stretch sensor longitudinally spans the dorsal surface of an elbow and/or the ventral surface of a knee. Alternatively, smart clothing can comprise: an article of clothing worn over a person's arm and/or leg; and an electromagnetic stretch (or bend) sensor printed onto the article of clothing with a PDMS-based ink which has been impregnated (or doped) with aluminum (or aluminum alloy) particles or pieces; wherein the stretch sensor longitudinally spans the dorsal surface of an elbow and/or the ventral surface of a knee.

In an example, smart clothing can comprise: an article of clothing which is configured to be worn over a person's arm and/or leg; and an EMG sensor comprising acrylic (yarn, thread, or fiber) coated (or embedded) with aluminum (or aluminum alloy) particles or pieces; wherein the EMG sensor spans between 5% and 55% of the circumference of the arm or leg. In an example, it can span between 25% and 50% of the circumference of the arm or leg. Alternatively, smart clothing can comprise: an article of clothing worn over a person's arm and/or leg; and an EMG sensor comprising cellulose, hydroxypropyl cellulose, and/or HPMC impregnated (or doped, embedded, or coated) with gold (or gold alloy); wherein the EMG sensor spans between 10% and 60% of the circumference of the arm or leg. Smart clothing can comprise: an article of clothing which is configured to be worn over a person's arm and/or leg; and an EMG sensor comprising hydrogel impregnated (or doped, embedded, or coated) with gallium; wherein the EMG sensor spans between 5% and 55% of the circumference of the arm or leg. Alternatively, smart clothing can comprise: an article of clothing worn over a person's arm and/or leg; and an EMG sensor comprising nylon (thread or yarn) coated (or embedded) with carbon (particles, nanotubes, microstructures, graphene, graphite); wherein the EMG sensor spans between 10% and 60% of the circumference of the arm or leg. Smart clothing can comprise: an article of clothing worn over a person's arm and/or leg; and an EMG sensor comprising polystyrene (PST) impregnated (or doped, embedded, or coated) with carbon (particles, nanotubes, microstructures, graphene, graphite); wherein the EMG sensor spans between 10% and 60% of the circumference of the arm or leg. Smart clothing can comprise: an article of clothing worn over a person's arm and/or leg; and an EMG sensor comprising PVOH impregnated (or doped, embedded, or coated) with nickel (or nickel alloy) particles or pieces; wherein the EMG sensor spans between 10% and 60% of the circumference of the arm or leg.

In another example, smart clothing can comprise: an article of clothing worn over a person's arm and/or leg; and an EMG sensor comprising silicone, silicone rubber, and/or PDMS impregnated (or doped, embedded, or coated) with gold (or gold alloy); wherein the EMG sensor spans between 10% and 60% of the circumference of the arm or leg. Alternatively, smart clothing can comprise: an article of clothing worn over a person's arm and/or leg; and an EMG sensor comprising stretchable thread or yarn coated (or embedded) with conductive metal particles, pieces, or microstructures; wherein the EMG sensor spans between 10% and 60% of the circumference of the arm or leg. Alternatively, smart clothing can comprise: an article of clothing which is configured to be worn over a person's arm and/or leg; and an EMG sensor printed onto the article of clothing with a polymer-based ink which has been impregnated (or doped) with conductive metal particles, pieces, or microstructures; wherein the EMG sensor spans between 10% and 60% of the circumference of the arm or leg. Smart clothing can comprise: an article of clothing worn over a person's arm and/or leg; and an EMG sensor printed onto the article of clothing with conductive ink or resin which has been impregnated (or doped) with niobium; wherein the EMG sensor spans between 10% and 60% of the circumference of the arm or leg. Smart clothing can comprise: an article of clothing; and an EMG sensor comprising cotton (thread or fiber) coated (or embedded) with gallium; wherein the EMG sensor is woven, sewn, or embroidered into the article of clothing. Smart clothing can comprise: an article of clothing; and an EMG sensor comprising nylon (thread or yarn) coated (or embedded) with copper (or copper alloy) particles or pieces; wherein the EMG sensor is woven, sewn, or embroidered into the article of clothing.

In an example, smart clothing can comprise: an article of clothing; and an EMG sensor comprising wool yarn coated (or embedded) with copper (or copper alloy) particles or pieces; wherein the EMG sensor is woven, sewn, or embroidered into the article of clothing. Smart clothing can comprise: an article of clothing; and an EMG sensor comprising cellulose, hydroxypropyl cellulose, and/or HPMC impregnated (or doped, embedded, or coated) with silver (or sliver alloy, silver chloride); wherein the EMG sensor is sewn onto, woven into, adhered to, inserted into, or otherwise attached to the article of clothing. Alternatively, smart clothing can comprise: an article of clothing; and an EMG sensor comprising PEDOT/PSS impregnated (or doped, embedded, or coated) with niobium; wherein the EMG sensor is sewn onto, woven into, adhered to, inserted into, or otherwise attached to the article of clothing. Smart clothing can comprise: an article of clothing; and an EMG sensor comprising polypropylene glycol impregnated (or doped, embedded, or coated) with gallium; wherein the EMG sensor is sewn onto, woven into, adhered to, inserted into, or otherwise attached to the article of clothing. Alternatively, smart clothing can comprise: an article of clothing; and an EMG sensor comprising silicone, silicone rubber, and/or PDMS impregnated (or doped, embedded, or coated) with gallium; wherein the EMG sensor is sewn onto, woven into, adhered to, inserted into, or otherwise attached to the article of clothing. Alternatively, smart clothing can comprise: an article of clothing; and an EMG sensor comprising TPE, TPU, and/or TPV impregnated (or doped, embedded, or coated) with steel particles or pieces; wherein the EMG sensor is sewn onto, woven into, adhered to, inserted into, or otherwise attached to the article of clothing.

In another example, smart clothing can comprise: an article of clothing; and an EMG sensor comprising an elastic material and/or an elastomeric polymer impregnated (or doped, embedded, or coated) with silver (or sliver alloy, silver chloride) particles or pieces. Smart clothing can comprise: an article of clothing; and an EMG sensor comprising cotton (thread or fiber) coated (or embedded) with gold (or gold alloy) particles or pieces. Smart clothing can comprise: an article of clothing; and an EMG sensor comprising PEDOT/PSS impregnated (or doped, embedded, or coated) with gold (or gold alloy) particles or pieces. Alternatively, smart clothing can comprise: an article of clothing; and an EMG sensor comprising PEG, PET, or PTFE impregnated (or doped, embedded, or coated) with tungsten particles or pieces. Smart clothing can comprise: an article of clothing; and an EMG sensor comprising polyurethane impregnated (or doped, embedded, or coated) with steel particles or pieces. Alternatively, smart clothing can comprise: an article of clothing; and an EMG sensor comprising rayon (thread or yarn) coated (or embedded) with nickel (or nickel alloy) particles or pieces.

In an example, smart clothing can comprise: an article of clothing; and an EMG sensor comprising SEBS impregnated (or doped, embedded, or coated) with nickel (or nickel alloy) particles or pieces. Smart clothing can comprise: an article of clothing; and an EMG sensor printed onto the article of clothing with a PDMS-based ink which has been impregnated (or doped) with aluminum (or aluminum alloy) particles or pieces. Smart clothing can comprise: an article of clothing; and an EMG sensor printed onto the article of clothing with a silicone-based ink which has been impregnated (or doped) with tungsten particles or pieces. Smart clothing can comprise: an article of clothing worn over a person's arm and/or leg; and an electromagnetic stretch (or bend) sensor comprising acrylic (yarn, thread, or fiber) coated (or embedded) with gold (or gold alloy); wherein the stretch sensor spirals around an elbow and/or a knee. Alternatively, smart clothing can comprise: an article of clothing worn over a person's arm and/or leg; and an electromagnetic stretch (or bend) sensor comprising cellulose, hydroxypropyl cellulose, and/or HPMC impregnated (or doped, embedded, or coated) with copper (or copper alloy); wherein the stretch sensor spirals around an elbow and/or a knee. Smart clothing can comprise: an article of clothing worn over a person's arm and/or leg; and an electromagnetic stretch (or bend) sensor comprising cotton (thread or fiber) coated (or embedded) with nickel (or nickel alloy) particles or pieces; wherein the stretch sensor spirals around an elbow and/or a knee.

I claim:

1. A device or system for capturing human motion comprising:

an article of clothing worn by a person, wherein a portion of the article of clothing has a longitudinal axis which is configured to span a body joint, wherein the portion has a first cross-sectional circumference which is proximal relative to the body joint, wherein the portion has a second cross-sectional circumference which is distal relative to the body joint, and wherein proximal means closer to and distal means farther from the person's heart when the person is in Vitruvian Man configuration;

a first inertial motion sensor which is incorporated into the portion at the first cross-sectional circumference;

a second inertial motion sensor which is incorporated into the portion at the second cross-sectional circumference;

a first strain sensor which is incorporated into the portion and spans the body joint between the first cross-sectional circumference and the second cross-sectional circumference, wherein the first strain sensor collects data concerning the transmission of electromagnetic energy through the first strain sensor;

a second strain sensor which is incorporated into the portion and spans the body joint between the first cross-sectional circumference and the second cross-sectional circumference, wherein the second strain sensor collects data concerning the transmission of electromagnetic energy through the second strain sensor;

an electromyographic sensor which is incorporated into the portion and is in electromagnetic communication with a muscle which moves the body joint and/or with nerves which innervate the muscle, and wherein the electromyographic sensor collects data concerning electromagnetic energy emitted by the muscle and/or the nerves; and a data processor which analyzes data from the first inertial motion sensor, the second inertial motion sensor, the first strain sensor, the second strain sensor, and the electromyographic sensor to measure a configuration and/or motion of the body joint.

2. A device or system for capturing human motion comprising:

an article of clothing worn by a person, wherein a portion of the article of clothing has a longitudinal axis which is configured to span a body joint, wherein the portion has a first cross-sectional circumference which is proximal relative to the body joint, wherein the portion has a second cross-sectional circumference which is distal relative to the body joint, and wherein proximal means closer to and distal means farther from the person's heart when the person is in Vitruvian Man configuration;

a first inertial motion sensor which is incorporated into the portion at the first cross-sectional circumference;

a second inertial motion sensor which is incorporated into the portion at the second cross-sectional circumference;

a first strain sensor which is incorporated into the portion and spans the body joint at a first angle relative to the longitudinal axis, wherein the first strain sensor collects data concerning the transmission of electromagnetic energy through the first strain sensor;

a second strain sensor which is incorporated into the portion and spans the body joint at a second angle relative to the longitudinal axis, wherein the second angle is rotated between 10 and 50 degrees relative to the first angle, and wherein the second strain sensor collects data concerning the transmission of electromagnetic energy through the second strain sensor;

an electromyographic sensor which is incorporated into the portion and is in electromagnetic communication with a muscle which moves the body joint and/or with nerves which innervate the muscle, and wherein the electromyographic sensor collects data concerning electromagnetic energy emitted by the muscle and/or the nerves; and a data processor which analyzes data from the first inertial motion sensor, the second inertial motion sensor, the first strain sensor, the second strain sensor, and the electromyographic sensor to measure a configuration and/or motion of the body joint.

3. A device or system for capturing human motion comprising:

an article of clothing worn by a person, wherein a portion of the article of clothing has a longitudinal axis which is configured to span a body joint, wherein the portion has a first cross-sectional circumference which is proximal relative to the body joint, wherein the portion has a second cross-sectional circumference which is distal relative to the body joint, and wherein proximal means closer to and distal means farther from the person's heart when the person is in Vitruvian Man configuration;

a first inertial motion sensor which is incorporated into the portion at the first cross-sectional circumference;

a second inertial motion sensor which is incorporated into the portion at the second cross-sectional circumference;

a first strain sensor made with an elastomeric silicone-based polymer which has been doped, impregnated, or coated with electroconductive material and is incorporated into the portion and spans the body joint between the first cross-sectional circumference and the second cross-sectional circumference, wherein the first strain sensor collects data concerning the transmission of electromagnetic energy through the first strain sensor;

a second strain sensor made with an elastomeric silicone-based polymer which has been doped, impregnated, or coated with electroconductive material and is incorporated into the portion and spans the body joint between the first cross-sectional circumference and the second cross-sectional circumference, wherein the second strain sensor collects data concerning the transmission of electromagnetic energy through the second strain sensor;

an electromyographic sensor which is incorporated into the portion and is in electromagnetic communication with a muscle which moves the body joint and/or with nerves which innervate the muscle, and wherein the electromyographic sensor collects data concerning electromagnetic energy emitted by the muscle and/or the nerves; and a data processor which analyzes data from the first inertial motion sensor, the second inertial motion sensor, the first strain sensor, the second strain sensor, and the electromyographic sensor to measure a configuration and/or motion of the body joint.

* * * * *